US010279103B2

(12) United States Patent
Okihara

(10) Patent No.: US 10,279,103 B2
(45) Date of Patent: May 7, 2019

(54) OUTER CYLINDER FOR PREFILLED SYRINGE AND OUTER CYLINDER PACKAGING FOR PREFILLED SYRINGES

(71) Applicant: Terumo Kabushiki Kaisha, Tokyo (JP)

(72) Inventor: Hitoshi Okihara, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 607 days.

(21) Appl. No.: 14/662,959

(22) Filed: Mar. 19, 2015

(65) Prior Publication Data

US 2015/0190566 A1    Jul. 9, 2015

Related U.S. Application Data

(63) Continuation of application No. PCT/JP2012/083980, filed on Dec. 27, 2012.

(51) Int. Cl.
*A61M 5/31* (2006.01)
*A61M 5/00* (2006.01)
(Continued)

(52) U.S. Cl.
CPC ........... *A61M 5/002* (2013.01); *A61M 5/001* (2013.01); *A61M 5/008* (2013.01);
(Continued)

(58) Field of Classification Search
CPC ........ A61M 5/002; A61M 5/008; A61M 5/34; A61M 5/3202; A61M 5/3134; A61M 5/3135; A61M 5/344; A61M 2005/3104
(Continued)

(56) References Cited

U.S. PATENT DOCUMENTS 4,929,232 A * 5/1990 Sweeney ............. A61M 5/3202
604/111
6,164,044 A * 12/2000 Porfano ................. B65B 55/10
422/28

(Continued)

FOREIGN PATENT DOCUMENTS

EP    2 119 463 A1    11/2009
EP    2 332 601 A1     6/2011
(Continued)

OTHER PUBLICATIONS

International Search Report dated Apr. 9, 2013 in PCT/JP2012/083980 with English-language translation (4 pgs.).
(Continued)

*Primary Examiner* — Steven A. Reynolds
(74) *Attorney, Agent, or Firm* — Foley & Lardner LLP

(57) ABSTRACT

A outer cylinder packaging for prefilled syringes includes a container having an upper face that has an upper face opening; an outer cylinder holding member that is located in the container and includes at least one outer cylinder holding opening part; at least one outer cylinder for prefilled syringe that is held by the outer cylinder holding member; and a removable sheet-shaped lid member that seals the upper face opening of the container. The outer cylinder for prefilled syringe includes: an outer cylinder main body part; a flange part; a nozzle part that is provided at a tip part of the outer cylinder main body part and has a tip opening part at its tip; and a distal cylindrical part that covers the nozzle part, has a diameter that is larger than an outer diameter of the outer cylinder main body part, and passes through the outer cylinder holding opening part.

6 Claims, 28 Drawing Sheets

(51) Int. Cl.
*A61M 5/32* (2006.01)
*A61M 5/34* (2006.01)

(52) U.S. Cl.
CPC ........ *A61M 5/3134* (2013.01); *A61M 5/3135* (2013.01); *A61M 5/3202* (2013.01); *A61M 5/34* (2013.01); *A61M 5/344* (2013.01); *A61M 2005/312* (2013.01); *A61M 2005/3104* (2013.01)

(58) Field of Classification Search
USPC ........ 206/366, 443, 364, 365; 604/256, 111; 211/60.1, 74
See application file for complete search history.

(56) References Cited

U.S. PATENT DOCUMENTS

| | | | | |
|---|---|---|---|---|
| 6,190,364 | B1* | 2/2001 | Imbert | A61M 5/3134 604/111 |
| 6,196,998 | B1* | 3/2001 | Jansen | A61M 5/3134 604/111 |
| 6,585,691 | B1* | 7/2003 | Vitello | A61M 5/3134 215/230 |
| 7,674,555 | B2* | 3/2010 | Nanba | H01M 4/0471 252/182.1 |
| 9,468,711 | B2* | 10/2016 | Iwase | A61M 5/008 |
| 9,649,449 | B2* | 5/2017 | Glocker | A61M 5/3202 |
| 2007/0151882 | A1* | 7/2007 | Cocheteux | A61M 5/008 206/366 |
| 2010/0012546 | A1* | 1/2010 | Togashi | A61M 5/008 206/534.1 |
| 2012/0109072 | A1 | 5/2012 | Tabata et al. | |
| 2012/0118777 | A1* | 5/2012 | Kakiuchi | A61M 5/002 206/366 |
| 2013/0001117 | A1* | 1/2013 | Liversidge | A61M 5/008 206/364 |

FOREIGN PATENT DOCUMENTS

| | | |
|---|---|---|
| EP | 2 818 190 A1 | 12/2014 |
| JP | 2002-210011 A | 7/2002 |
| JP | 2005-230458 A | 9/2005 |
| JP | 2012-071046 A | 4/2012 |
| WO | WO 2010/024209 A1 | 3/2010 |
| WO | WO-2010/081838 A2 | 7/2010 |
| WO | WO-2012/035155 A1 | 3/2012 |

OTHER PUBLICATIONS

European Patent Office, "Communication with Extended European Search Report," issued in connection with European Patent Application No 12 890 916.5, dated Jun. 16, 2016.

English language translation of "The First Office Action," issued by the State Intellectual Property Office of People's Republic of China in connection with Chinese Patent Application No 201280075680.2, dated Jun. 15, 2016.

English language translation of the "Decision to Grant a Patent," issued by the Japanese Patent Office in connection with Japanese Patent Application No. 2014-553979, dated Mar. 15, 2016.

The International Bureau of WIPO, "International Preliminary Report on Patentability," issued in connection with International Patent Application No. PCT/JP2012/083980, dated Jun. 30, 2015.

* cited by examiner

Fig.32
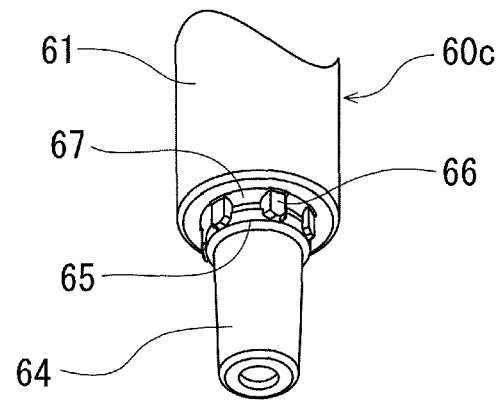
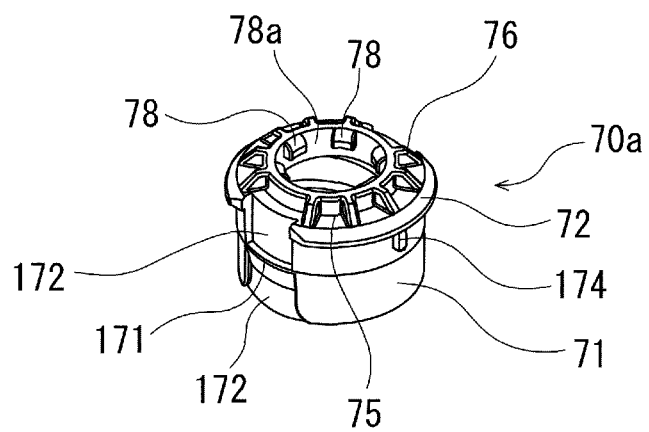
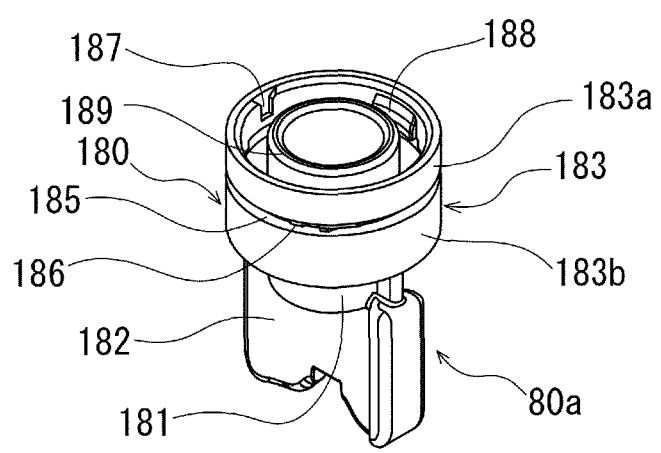

OUTER CYLINDER FOR PREFILLED SYRINGE AND OUTER CYLINDER PACKAGING FOR PREFILLED SYRINGES

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/083980 filed Dec. 27, 2012, the entire contents of which is hereby incorporated by reference in its entirety.

BACKGROUND

Technical Field

The present disclosure relates to an outer cylinder for prefilled syringe and an outer cylinder packaging for prefilled syringes.

Background Art

In JP 2012-71046 A, an outer cylinder packaging for prefilled syringes for storing a plurality of outer cylinders for prefilled syringes that are sterilizable or sterilized is provided for carrying the outer cylinders for prefilled syringes before being filled with a medicinal solution or the like. As a usage example of such an outer cylinder packaging for prefilled syringes, the outer cylinders for prefilled syringes are inserted into plural cylindrical parts that are provided in an outer cylinder holding member so as to be held thereby and are carried together with the packaging to a place to fill the medicinal solution or the like. Then, the outer cylinders for prefilled syringes are withdrawn one by one from the cylindrical parts of the outer cylinder holding member before being filled with the medicinal solution or the like.

FIGS. 2 and 6 of JP 2012-71046 A disclose as follows. In an outer cylinder for prefilled syringe 6, a flange part of which diameter is larger than that of an outer cylinder main body part 61 is formed at a proximal side of the cylinder main body part 61. The outer diameter of the outer cylinder main body part 61 of the outer cylinder for prefilled syringe 6 is smaller than an inner diameter of a cylindrical part 42 that protrudes upward from a substrate part 41 of an outer cylinder holding member 4 and is smaller than an inner diameter of an outer cylinder holding opening part 45 at an upper end of the cylindrical part 42. The outer cylinder for prefilled syringe 6 is held by the outer cylinder holding member 4 in a state where this outer cylinder main body part 61 is inserted into the cylindrical part 42 from above and the flange part is locked with and suspended by the outer cylinder holding opening part 45. The outer cylinder for prefilled syringe 6 in the thus suspended state is withdrawn from the cylindrical part 42 of the outer cylinder main body part 61 by gripping the flange part before being filled with the medicinal solution.

In JP 2012-71046 A, a cap 80 for sealing a nozzle part is attached to the nozzle part that is at a tip of the outer cylinder main body part 61 of the outer cylinder for prefilled syringe 6. For attaching this cap 80 to the outer cylinder main body part 61, a means or the like for being screwed with the cap 80 via a cylindrical member such as a lock adapter, which has a screw part formed thereto, is used. Then, an outer diameter of this lock adapter or the like is set to be smaller than the inner diameter of the above-described cylindrical part 42 and the inner diameter of the outer cylinder holding opening part 45 so that the lock adapter or the like can pass through the cylindrical part 42. Thus, in the state where the cylindrical member such as the lock adapter, together with the tip of the outer cylinder for prefilled syringe 6, is inserted downward more than an opening part that is at a lower end of the cylindrical part 42, the outer cylinder for prefilled syringe 6 is held by the outer cylinder holding member 4.

However, in a case where a volume of the medicinal solution to be filled is small, the outer diameter of the outer cylinder main body part 61 becomes small, and the outer diameter of the member such as the lock adapter becomes larger than that of the outer cylinder main body part 61, so that the member such as the lock adapter comes to have a step part with respect to the outer cylinder main body part 61. In such a case, when withdrawing the prefilled syringe from the cylindrical part 42 of the outer cylinder holding member 4, the step part of the member such as the lock adapter is likely to be caught by the opening at the lower end of the cylindrical part 42. Therefore, the withdrawal operation of the prefilled syringe cannot be carried out smoothly, and the lock adapter may be damaged.

SUMMARY OF INVENTION

One objective of certain embodiments of the present invention is to provide an outer cylinder for prefilled syringe and an outer cylinder packaging for prefilled syringes that enable smooth withdrawal of the outer cylinder for prefilled syringe by reducing a risk that the outer cylinder for prefilled syringe is caught by the outer cylinder holding member of the outer cylinder packaging for prefilled syringes during the withdrawal of the outer cylinder for prefilled syringe.

In one embodiment, an outer cylinder packaging for prefilled syringes that stores at least one outer cylinder for prefilled syringe and is sterilizable or sterilized includes a container having an upper face that has an upper face opening; an outer cylinder holding member that is located in the container and includes at least one outer cylinder holding opening part; at least one outer cylinder for prefilled syringe that is held by the outer cylinder holding member; and a removable sheet-shaped lid member that seals the upper face opening of the container. The at least one outer cylinder for prefilled syringe includes: an outer cylinder main body part; a flange part that is provided at a proximal part of the outer cylinder main body part, protrudes outward, and is not passable through the outer cylinder holding opening part; a nozzle part that is provided at a tip part of the outer cylinder main body part and has a tip opening part at its tip; and a distal cylindrical part that covers the nozzle part, has a diameter that is larger than an outer diameter of the outer cylinder main body part, and passes through the outer cylinder holding opening part. The at least one outer cylinder for prefilled syringe is located in the at least one outer cylinder holding opening part of the outer cylinder holding member such that the flange part of the at least one outer cylinder for prefilled syringe is in contact with and suspended by a rim of the at least one outer cylinder holding opening part. The at least one outer cylinder for prefilled syringe includes an inclined part that is positioned at a proximal part of the distal cylindrical part and is inclined in a proximal direction from an outer edge of the distal cylindrical part toward an outer peripheral face of the outer cylinder main body part so as to guide the at least one outer cylinder for prefilled syringe to be withdrawn from the at least one outer cylinder holding opening part.

In one aspect, the at least one outer cylinder for prefilled syringe further includes a cap that is attached to a tip part of the outer cylinder for prefilled syringe and that seals the tip opening part of the nozzle part, the nozzle part is configured such that a medical instrument is connectable thereto, the distal cylindrical part further includes, on its inner peripheral face, a cylindrical part-side screw part that is screwably connectable to the medical instrument that is to be connected to the nozzle part, and the cap is passable through the outer cylinder holding opening part.

In one aspect, the distal cylindrical part further includes: a cylindrical main body part; and an annular proximal part that is positioned proximal of the cylindrical main body part. The inclined part is formed of a proximal face of the annular proximal part. An outer edge of a tip part of the annular proximal part protrudes farther outward than an outer peripheral face of the cylindrical main body part. The cap includes an attachment part that covers the outer peripheral face of the cylindrical main body part.

In one aspect, the attachment part of the cap includes: an outside cylindrical part that covers the outer peripheral face of the cylindrical main body part; and an inside cylindrical part that is positioned inside the outside cylindrical part and has, on its outer peripheral face, a cap-side screw part that screwably connectable to the cylindrical part-side screw part. The cap further includes: a sealing member that is located in the inside cylindrical part and configured to seal the tip opening part of the nozzle part; and a rib that is formed on an inner face of the outside cylindrical part. The cap is configured to be attachable to the tip part of the outer cylinder for prefilled syringe by screwing together the cylindrical part-side screw part and the cap-side screw part. The distal cylindrical part further includes a protrusion part that is provided on the outer peripheral face of the cylindrical main body part. The cap is configured to inhibit looseness between the rib and the protrusion part by way of a contact between the rib and the protrusion part when the cap is attached to the outer cylinder for prefilled syringe.

In one aspect, when the cap is attached to the outer cylinder for prefilled syringe, an inner face of the rib of the cap and an outer face of the protrusion part of the distal cylindrical part contact each other. One of the container and the sheet-shaped lid member includes a ventilation part that has bacteria impermeability and vapor distributability. The at least one outer cylinder for prefilled syringe is sterilizable by high pressure steam while stored in the outer cylinder packaging for prefilled syringes.

In another embodiment, an outer cylinder for prefilled syringe configured to be stored in a container that includes an upper face that has an opening, an outer cylinder holding member that is stored in the container and includes at least one outer cylinder holding opening part; and a removable sheet-shaped lid member that seals the upper face opening of the container, includes: an outer cylinder main body part; a flange part that is provided at a proximal part of the outer cylinder main body part, protrudes outward, and is not passable through the outer cylinder holding opening part; a nozzle part that is provided at a tip part of the outer cylinder main body part and has a tip opening part at its tip; and a distal cylindrical part that covers the nozzle part, has a diameter that is larger than an outer diameter of the outer cylinder main body part, and is passable through the outer cylinder holding opening part. The outer cylinder for prefilled syringe is configured to be inserted into the outer cylinder holding opening part of the outer cylinder holding member. The outer cylinder for prefilled syringe includes an inclined part that is positioned at a proximal part of the distal cylindrical part and is inclined in a proximal direction from an outer edge of the distal cylindrical part toward an outer peripheral face of the outer cylinder main body part so as to guide the outer cylinder for prefilled syringe to be withdrawn from the outer cylinder holding opening part.

In one aspect, the outer cylinder for prefilled syringe further includes a cap that is attached to a tip part of the outer cylinder for prefilled syringe and seals the tip opening part of the nozzle part, and the nozzle part is configured such that a medical instrument is connectable thereto.

In one aspect, the distal cylindrical part further includes, on its inner peripheral face, a cylindrical part-side screw part that screwably connectable to the medical instrument that is to be connected to the nozzle part, and the cap is passable through the outer cylinder holding opening part.

In one aspect, the distal cylindrical part further includes: a cylindrical main body part; and an annular proximal part that is positioned proximal of the cylindrical main body part. The inclined part is formed of a proximal face of the annular proximal part.

In one aspect, an outer edge of a tip part of the annular proximal part protrudes farther outward than an outer peripheral face of the cylindrical main body part, and the cap includes an attachment part that covers the outer peripheral face of the cylindrical main body part.

In one aspect, the attachment part of the cap includes: an outside cylindrical part that covers the outer peripheral face of the cylindrical main body part; and an inside cylindrical part that is positioned inside the outside cylindrical part and has, on its outer peripheral face, a cap-side screw part that is screwably connectable to the cylindrical part-side screw part.

In one aspect, the cap further includes: a sealing member that is located in the inside cylindrical part and seals the tip opening part of the nozzle part; and a rib that is formed on an inner face of the outside cylindrical part.

In one aspect, the cap is configured to be attachable to the tip part of the outer cylinder for prefilled syringe by screwing together the cylindrical part-side screw part and the cap-side screw part.

In one aspect, the distal cylindrical part further includes a protrusion part that is provided on the outer peripheral face of the cylindrical main body part.

In one aspect, the cap is configured to inhibit looseness between the rib and the protrusion part by way of a contact between the rib and the protrusion part when the cap is attached to the outer cylinder for prefilled syringe.

BRIEF DESCRIPTION OF DRAWINGS

FIG. 32 is an explanatory drawing for explaining constituent members of the outer cylinder for prefilled syringe that is illustrated in FIG. 28.

DETAILED DESCRIPTION

Figure 1:
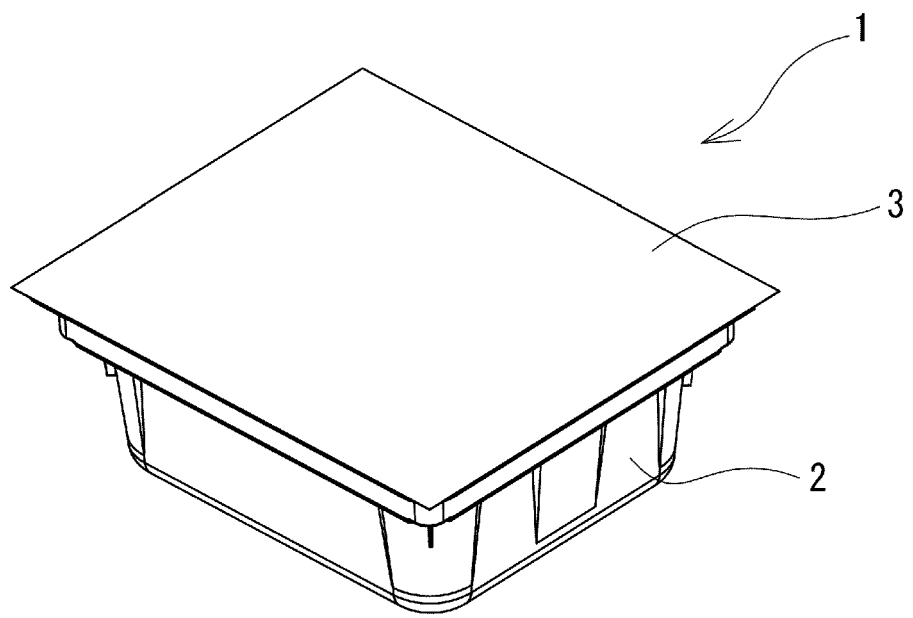
FIG. 1 is a perspective view of an outer cylinder packaging for prefilled syringes of a first embodiment of the present invention.

Hereinafter, a first embodiment of an outer cylinder for prefilled syringe and an outer cylinder packaging for prefilled syringes according to the present invention will be explained with reference to FIGS. 1 to 25.

A outer cylinder packaging for prefilled syringes 1 that stores plural outer cylinders for prefilled syringes and is sterilizable or sterilized includes: a container 2 of which an upper face has an opening and that has a shape retainable property; an outer cylinder holding member 4 that can hold the plural outer cylinders for prefilled syringes 6 stored in the container 2; the plural outer cylinders for prefilled syringes 6 that are held by the outer cylinder holding member 4; and a sheet-shaped lid member 3 that seals the upper face opening of the container 2 airtightly and can be peeled off.

The outer cylinder packaging for prefilled syringes 1 is an outer cylinder packaging for prefilled syringes that is sterilizable or sterilized. As a sterilizing method, high pressure steam sterilization, radiation or electron beam sterilization, or gas sterilization is used.

Figure 2:
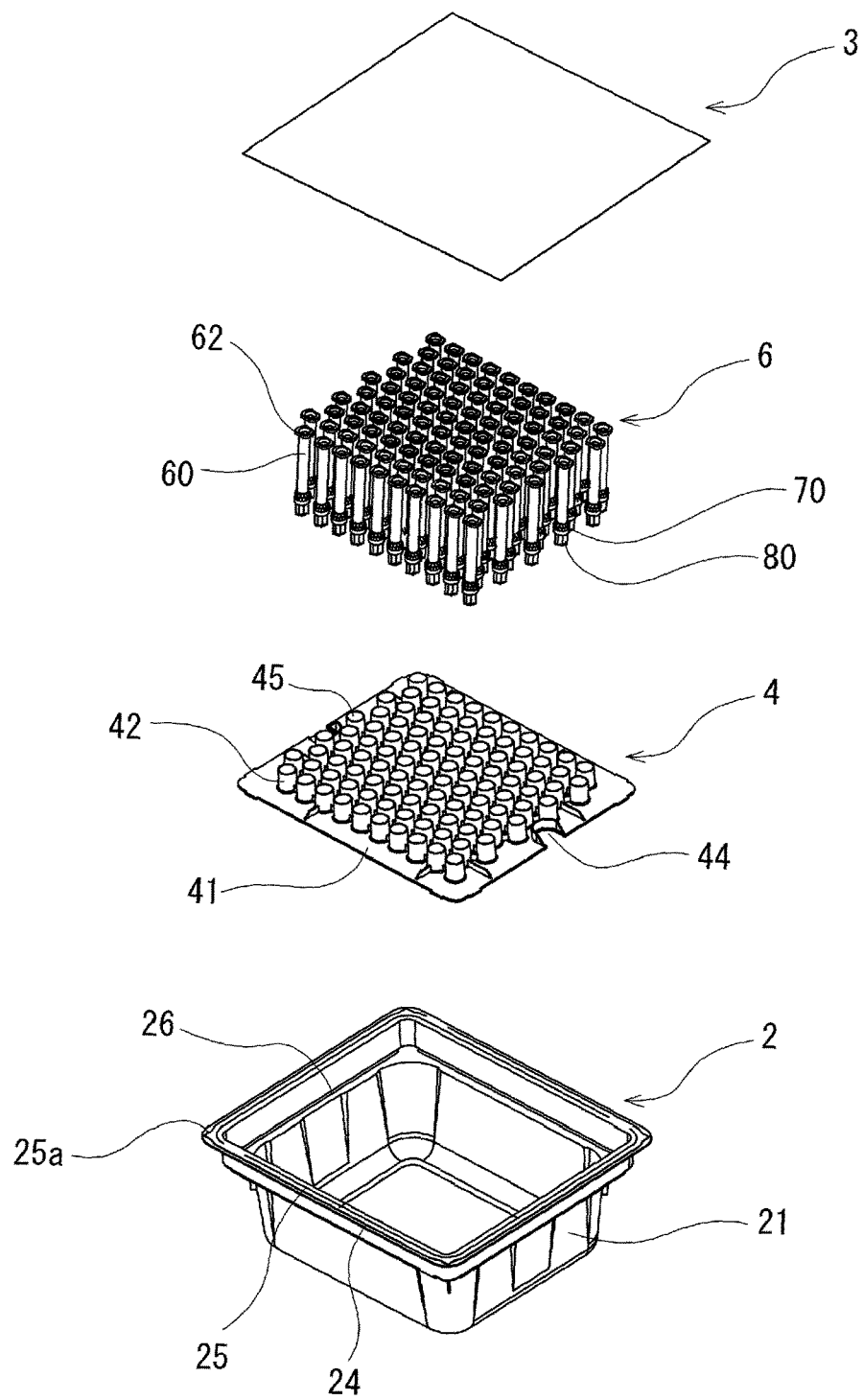
FIG. 2 is an explanatory drawing for explaining an internal configuration of the outer cylinder packaging for prefilled syringes that is illustrated in FIG. 1.
Figure 3:
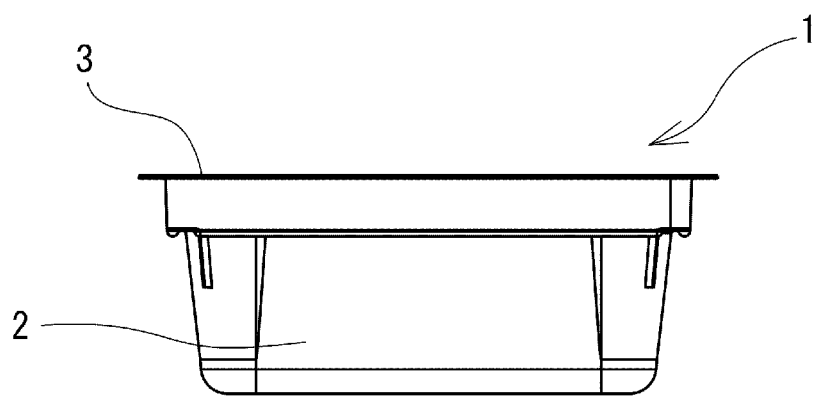
FIG. 3 is a front view of the outer cylinder packaging for prefilled syringes that is illustrated in FIG. 1.
Figure 4:
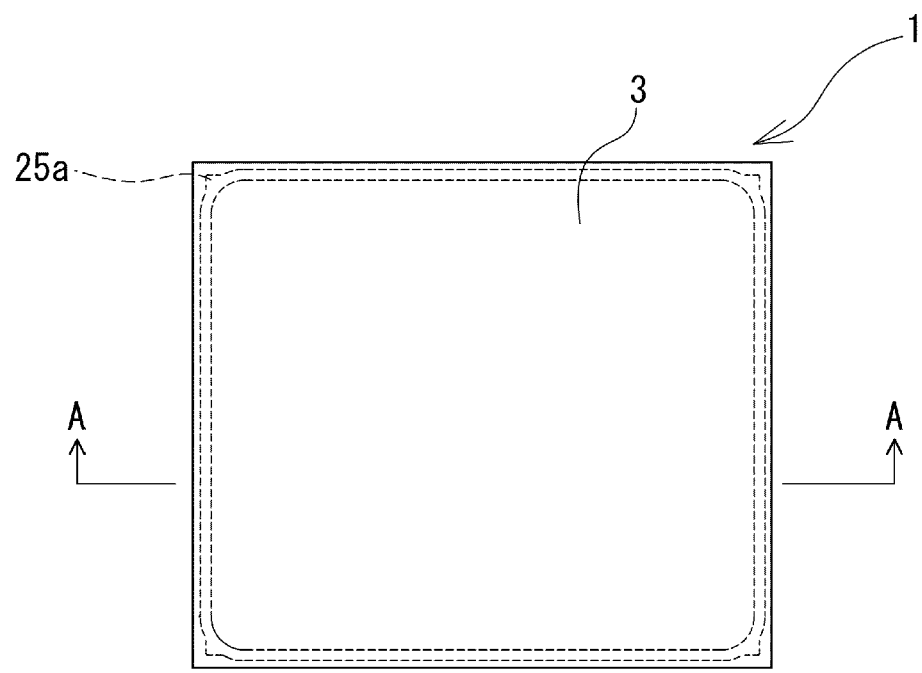
FIG. 4 is a plan view of the outer cylinder packaging for prefilled syringes that is illustrated in FIG. 3.
Figure 5:
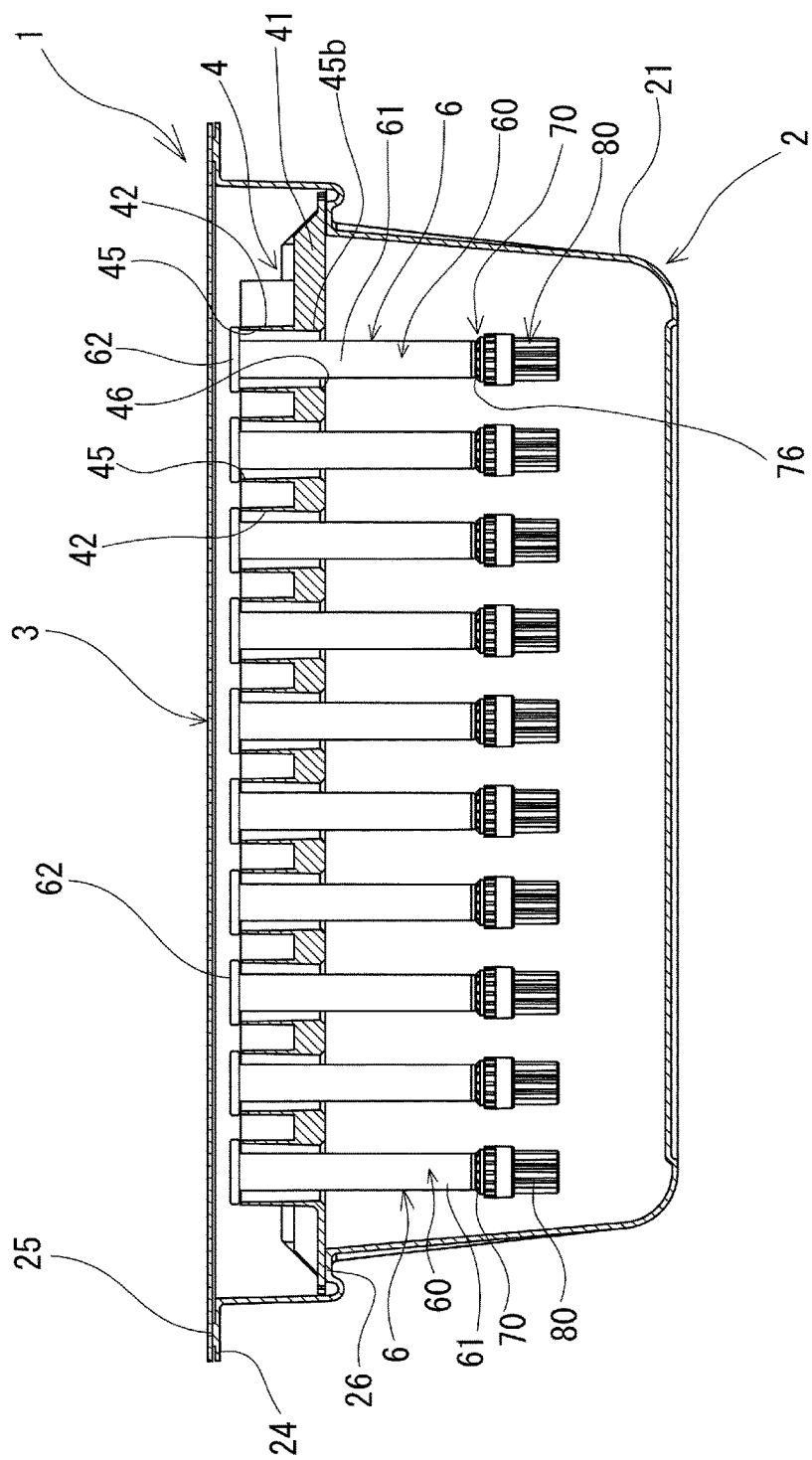
FIG. 5 is an enlarged cross-sectional view taken along a line A-A of FIG. 4.
Figure 6:
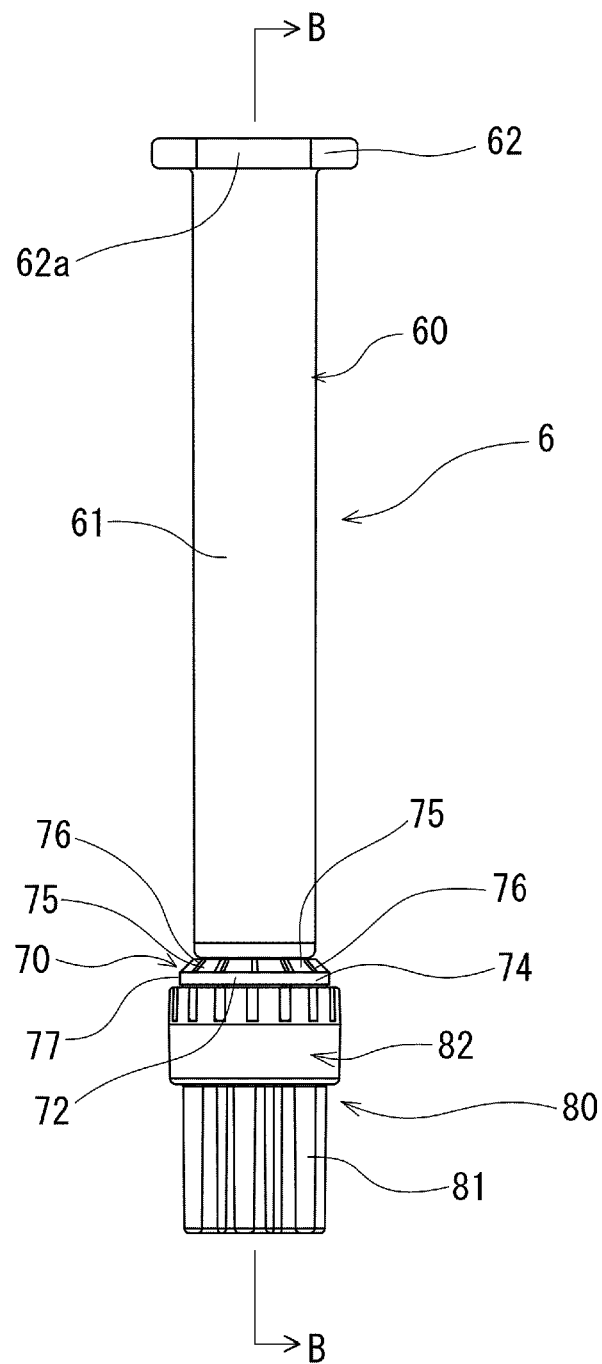
FIG. 6 is a front view of an outer cylinder for prefilled syringe of the first embodiment of the present invention.
Figure 7:
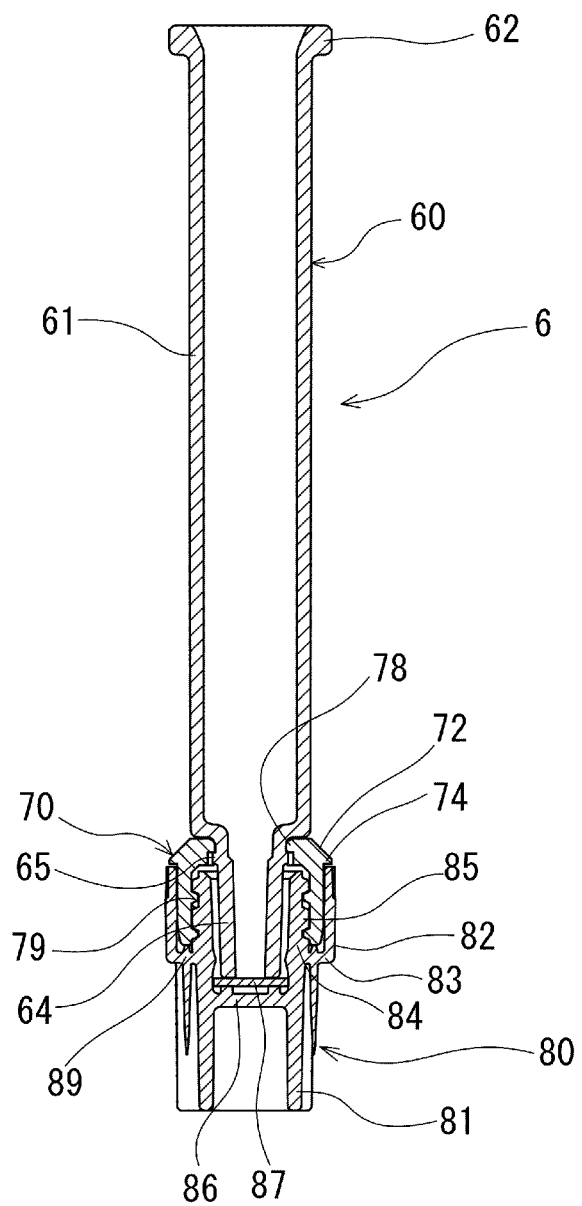
FIG. 7 is a cross-sectional view taken along a line B-B of FIG. 6.
Figure 8:
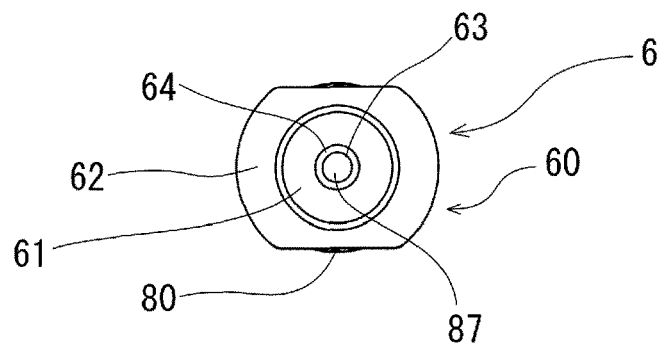
FIG. 8 is a plan view of the outer cylinder for prefilled syringe that is illustrated in FIG. 6.
Figure 9:
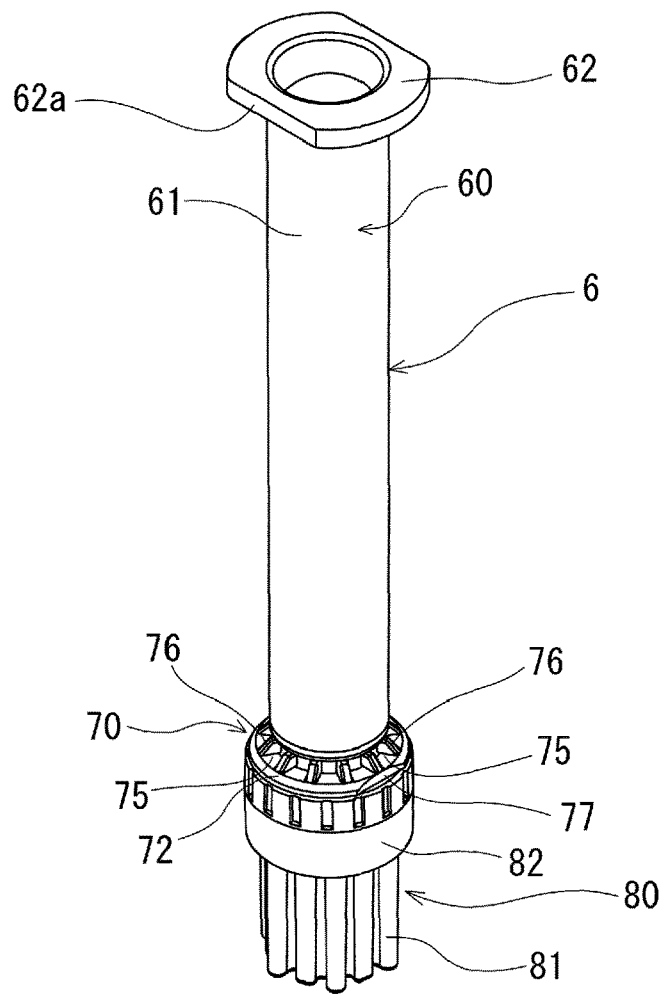
FIG. 9 is a perspective view of the outer cylinder for prefilled syringe that is illustrated in FIG. 6.
Figure 34:
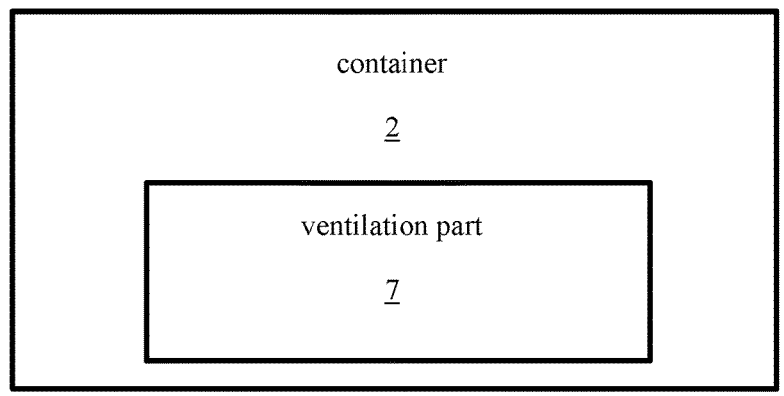
FIG. 34 is a box diagram showing a container that includes a ventilation part.
Figure 35:
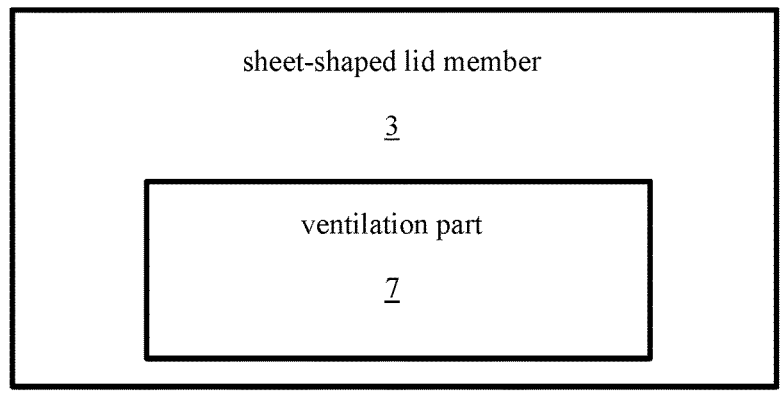
FIG. 35 is a box diagram showing a sheet-shaped lid member that includes a ventilation part.

As illustrated in FIGS. 1, 2 and 5, the outer cylinder packaging for prefilled syringes 1 includes: the container 2; the outer cylinder holding member 4 that can hold the plural outer cylinders for prefilled syringes 6; the plural outer cylinders for prefilled syringes 6 that are held by the outer cylinder holding member 4; and the sheet-shaped lid member 3 that seals the upper face opening of the container 2 airtightly and can be peeled off. Further, the packaging 1 includes a ventilation part 7 which is provided to the container 2 or the sheet-shaped lid member 3 and has bacteria impermeability and vapor distributability, as shown in the box diagram of FIGS. 34 and 35.

As illustrated in FIGS. 1 to 5, the container 2 has a tray shape with a predetermined depth, has a certain level of strength and a shape retainable property, and includes: a main body part 21; an outer cylinder holding member holding part 26 that is formed in an upper part of the main body part 21 in order to hold a rim part of the outer cylinder holding member 4 that holds the outer cylinder for prefilled syringe 6; and an annular flange 24 that is provided along the upper face opening.

Further, on an upper face of the annular flange 24, an annular heat-sealing convex part 25 to be fixed with the sheet-shaped lid member 3 is provided. Then, in a position that has a distance of a predetermined length from the flange 24 to a bottom face, the outer cylinder holding member holding part 26 is formed. In the container 2 of this first embodiment, the outer cylinder holding member holding part 26 is an annular step difference part, on which the rim part of the outer cylinder holding member 4 that holds the outer cylinder for prefilled syringe 6 can be placed.

The container 2 preferably has a certain level of a shape retainable property and rigidity. Further, in order to accommodate the high pressure steam sterilization, a thermoplastic material having heat resistance (120° C. or more) is preferably used for the container 2. Examples of the material that has the certain level of the shape retainable property, the certain level of the rigidity, the heat resistance, and the thermoplasticity include: polyolefin such as polypropylene and polyethylene; a vinyl chloride resin; a polystyrene/polypropylene resin; polyethylene/ionomer (for example, ethylene-based, styrene-based and fluorine-based)/polyethylene; a polyester resin (for example, polyethylene terephthalate, polybutylene terephthalate and amorphous polyethylene terephthalate); PP/EVOH/PP (a laminate); and the like. A thickness of the container 2 in this case preferably ranges from about 0.05 mm to about 4.00 mm, and in particular, more preferably ranges from 1.00 mm to 2.00 mm.

Moreover, the container 2 may be subjected to the radiation or electron beam sterilization, and in this case, so-called a radioresistant material is preferably used for the container 2. As the radioresistant material (for example, radioresistant polyolefin), polyolefin (for example, polypropylene or polyethylene) to which hindered amine and an antioxidant, a nucleating agent and the like are added so as to apply a radioresistant property can be used. Examples of the hindered amine include: bis(2,2,6,6-tetramethylpiperidyl) sebacate; bis(2,2,6,6-tetramethylpiperidyl) adipate; bis(2,2,6,6-tetramethylpiperidyl) fumarate; and the like. Examples of the antioxidant include: 1,1,3-tris(2-methyl-hydroxy-5-t-butylphenyl) butane; tris(3,5-di-t-butyl-4-hydroxybenzyl) isocyanurate; tetrakis(methylene-3-(3,5-di-t-butyl-4-hydroxyphenyl) propionate) methane; and the like. Examples of the nucleating agent include: 1,3:2,4-dibenzylidene sorbitol; 1,3,2,4-di(p-methylbenzylidene) sorbitol; and the like.

Figure 24:
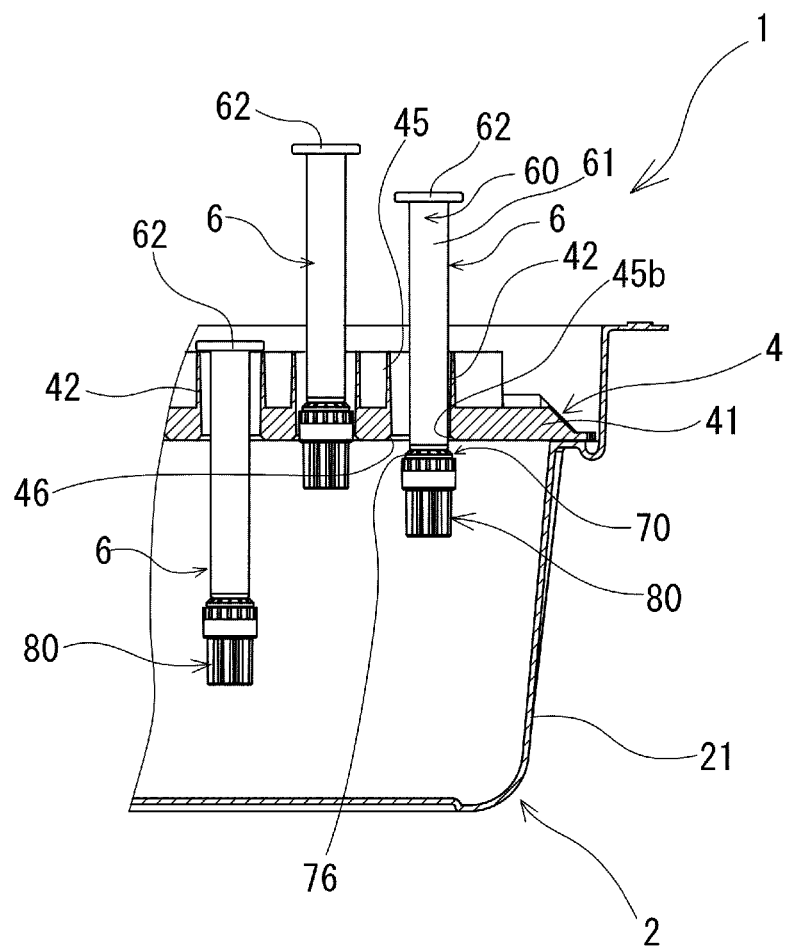
FIG. 24 is an explanatory drawing for explaining a withdrawal state of the outer cylinder for prefilled syringe of the outer cylinder packaging for prefilled syringes that is illustrated in FIG. 1.

As illustrated in FIGS. 2, 5 and 24, the outer cylinder holding member 4 that can hold the plural outer cylinders for prefilled syringes 6 includes: the substrate part 41; and the plural cylindrical parts 42 that protrude upward from this substrate part 41. Further, the outer cylinder holding opening part 45 is formed in the cylindrical part 42, and a notch part 44 for being gripped is formed in a lateral part of the substrate part 41. Along an opening 45b at a lower end of the outer cylinder holding opening part 45, an annular inclined face 46 of which inner diameter is increased toward the opening is provided. Inner diameters of the cylindrical part 42 and the outer cylinder holding opening part 45 are larger than an outer diameter of a maximum diameter part of the outer cylinder for prefilled syringe 6 that is to be held thereby, and the flange part of the outer cylinder for prefilled syringe 6 that is to be held thereby cannot pass through the cylindrical part 42 or the outer cylinder holding opening part 45.

Thus, as illustrated in FIG. 5, the outer cylinder 6 penetrates the cylindrical part 42 and is in a state where the flange of the outer cylinder is suspended by the outer cylinder holding opening part 45. Further, as shown in FIG. 5, a lower end (a tip of a cap member) of the outer cylinder for prefilled syringe 6 that is held by the outer cylinder holding member 4 does not contact with the bottom face of the container 2. In other words, the bottom face of the container 2 and the lower end (the tip of the cap member) of the outer cylinder for prefilled syringe 6 that is held by the outer cylinder holding member 4 are separated so as not to block distribution of vapor. In order to accommodate to the high pressure steam sterilization, this outer cylinder holding member 4 is preferably formed of a material that has the heat resistance (120° C. or more) as well.

As the sheet-shaped lid member 3, in order to accommodate to the high pressure steam sterilization, a member that does not allow fine particles such as bacteria and viruses to permeate but has vapor distributability is desirably used. Moreover, the member is preferably able to be heat-sealed with the container 2. As the sheet-shaped lid member 3, for example, a non-woven fabric made of a synthetic resin, more specifically, a non-woven fabric made of a synthetic resin material such as polyolefin, which is known as Tyvek (registered trademark), a porous film made of a synthetic resin or the like can be preferably used.

Further, a rim part of the sheet-shaped lid member 3 is heat-sealed with the heat-sealing convex part 25 that is provided on the annular flange 24 of the container 2 so that the rim part of the sheet-shaped lid member 3 can be peeled off. Incidentally, in this first embodiment, an outer edge of the sheet-shaped lid member 3 is not heat-sealed with the annular flange 24 of the container 2, and thus can be peeled off easily. Moreover, a protrusion part 25a that is provided at a corner part of the heat-sealing convex part 25 functions as an peeling starting part. A thickness of the sheet-shaped lid member 3 preferably ranges from about 0.05 mm to about 1.00 mm, and more preferably ranges from about 0.10 mm to about 0.50 mm.

Incidentally, although the ventilation part 7 is provided to the sheet-shaped lid member 3 in the above-described first embodiment, the ventilation part 7 is not limited to this, and may be provided to the container 2.

As illustrated in FIGS. 6 to 9, the outer cylinder for prefilled syringe 6 includes: an outer cylinder main body 60; a nozzle part 64 that is provided at a tip part of the outer cylinder main body 60 and has a tip opening part 63 at its tip; a lock adapter 70 that covers the nozzle part 64; and a cap 80 that seals the tip opening part 63 of the nozzle part 64. To the nozzle part 64, another medical instrument (for example, an injection needle, a connector or a three-way stopcock) can be connected. The cap 80 can pass through the outer cylinder holding opening part 45 of the outer cylinder holding member 4, as described below.

Figure 10:
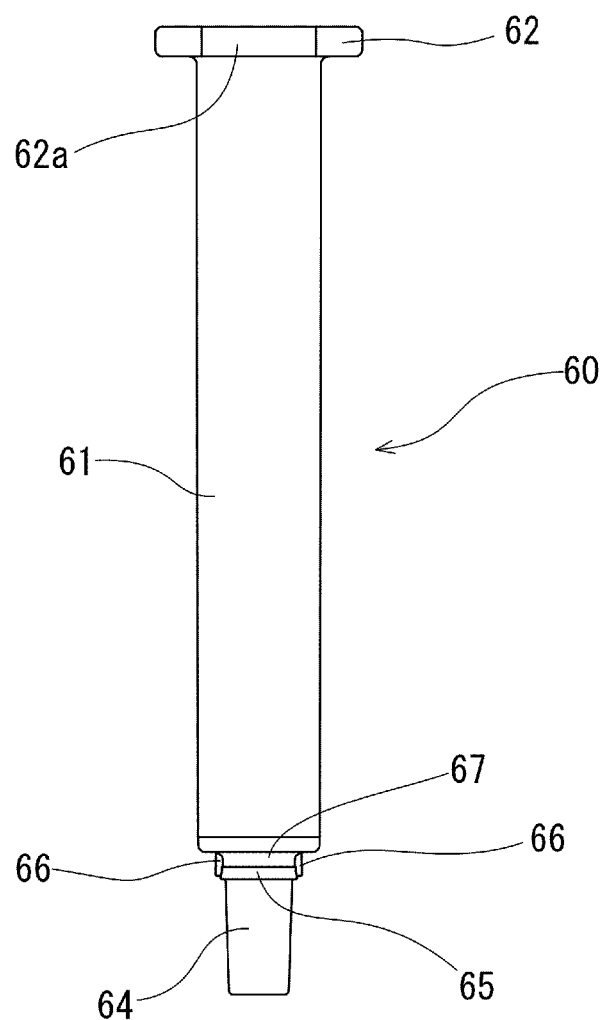
FIG. 10 is a front view of an outer cylinder main body used in the outer cylinder for prefilled syringe that is illustrated in FIG. 6.
Figure 11:
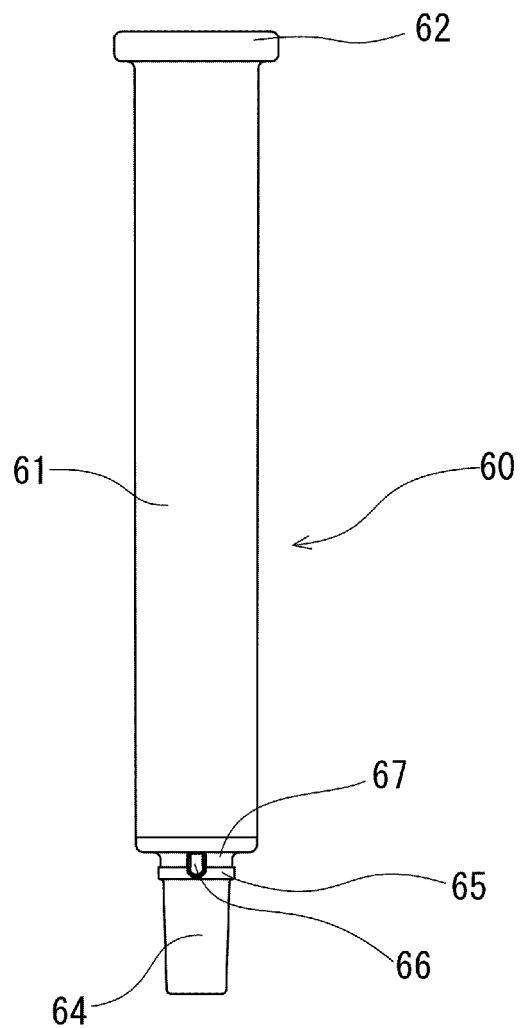
FIG. 11 is a right side view of the outer cylinder main body that is illustrated in FIG. 10.
Figure 12:
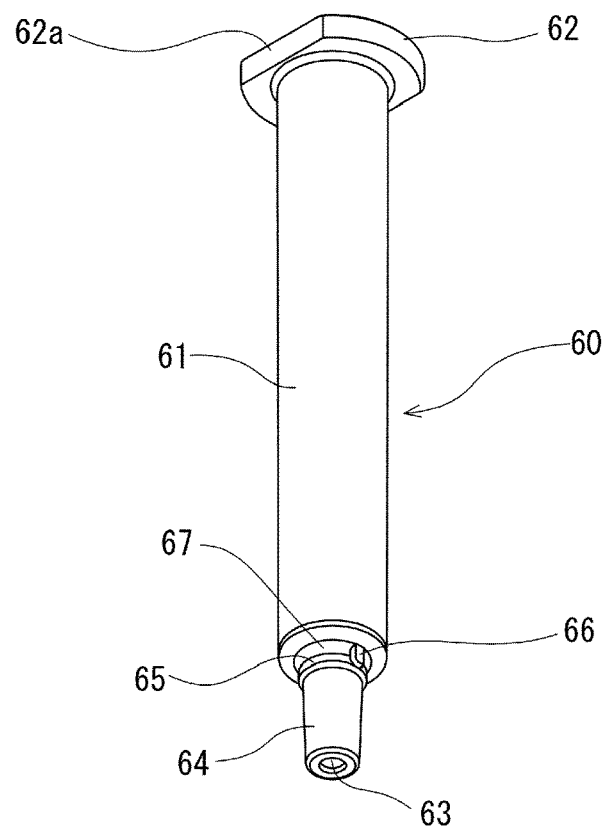
FIG. 12 is a perspective view of the outer cylinder main body that is illustrated in FIG. 10.

As illustrated in FIGS. 10 to 12, the outer cylinder main body 60 includes: the outer cylinder main body part 61; the nozzle part 64 that is provided on the distal of the outer cylinder main body part 61; and a flange 62 that is provided on a proximal side of the outer cylinder main body part 61. Incidentally, the lock adapter 70 corresponds to an example of the "distal cylindrical part" and the "cylindrical member". Further, in the outer cylinder for prefilled syringe 6 of this first embodiment, the distal cylindrical part includes, on its inner peripheral face, a cylindrical part-side screw part that can be screwed with the medical instrument (for example, a rib or a screw part that is formed along a flange of the injection needle, the connector, the three-way stopcock or the like) that is to be connected to the nozzle part 64 of the outer cylinder main body 60.

The outer cylinder main body part 61 of the outer cylinder main body 60 is formed in a cylindrical shape with a comparatively small diameter, which is to be filled with a small amount (specifically, ranging from 0.5 ml to 2 ml) of the medicinal solution or the like in this first embodiment, and the outer diameter of the outer cylinder main body part 61 ranges from 6 mm to 12 mm.

As illustrated in FIGS. 10 to 12, the flange 62 has an arc-shaped outer edge that is formed to protrude from whole circumference of the proximal side of the outer cylinder main body part 61 in a direction perpendicular to a central axis of the outer cylinder main body part 61. The flange 62 having the arc-shaped outer edge includes two linear parts 62a that are provided in substantially parallel so as to face each other. Further, the flange 62 has two arc-shaped outer edge parts that face each other. Moreover, the flange 62 includes: a short diameter part formed between the two linear parts 62a that are provided in substantially parallel so as to face each other; and a long diameter part formed between the two arc-shaped outer edge parts that face each other. Furthermore, the above-described short diameter part and the above-described long diameter part cross each other substantially perpendicularly.

As illustrated in FIGS. 10 to 12, the nozzle part 64 has a diameter that is smaller than the outer diameter of the outer cylinder main body part 61 and is decreased toward its tip. The nozzle part 64 has, at its tip, a tip opening part 63 for ejecting the medicinal solution or the like that is in the outer cylinder. Further, in the outer cylinder main body 60 of this first embodiment, the nozzle part 64 is provided with a locking rib 65 that can lock the below-described lock adapter 70 in its proximal part (on the slightly distal side from the tip of the outer cylinder main body part 61). Particularly in this first embodiment, the locking rib 65 is an annular rib. Incidentally, the locking rib 65 is preferably the annular rib, but may be plural short ribs that are arranged annularly. Moreover, between the locking rib 65 and the tip of the outer cylinder main body part 61, an annular concave part 67 is formed, and an annular protrusion part 78 of the lock adapter 70 is stored in this concave part 67. Furthermore, the annular protrusion part 78 is in contact with the locking rib 65, whereby detachment of the lock adapter 70 from the outer cylinder main body 60 is controlled.

Further, the proximal part of the nozzle part 64 is provided with rotation-controlling ribs 66. The rotation-controlling rib 66 is a short rib that is extended substantially parallel with the central axis of the outer cylinder main body part 61. In this first embodiment, the two rotation-controlling ribs 66 are provided so as to face each other. Moreover, corresponding to these rotation-controlling ribs 66, the annular protrusion part 78 of the lock adapter 70 is provided with notch parts 78a having a width that is larger than a transverse width of the rotation-controlling ribs 66 in order to store the rotation-controlling ribs 66. In this first embodiment, corresponding to the rotation-controlling ribs 66, the two notch parts 78a are also provided so as to face each other. The rotation-controlling ribs 66 of the outer cylinder main body 60 enter the notch parts 78a of the lock adapter 70, whereby rotation of the lock adapter 70 with respect to the outer cylinder main body 60 is controlled.

Examples of a material to form the outer cylinder main body 60 include various kinds of resins such as polypropylene, polyethylene, polystyrene, polyamide, polycarbonate, polyvinyl chloride, poly-(4-methyl pentene-1), an acrylic resin, acrylonitrile-butadiene-styrene copolymer, polyester such as polyethylene terephthalate, cyclic olefin polymer and cyclic olefin copolymer, and among them, the resins such as polypropylene, cyclic olefin polymer and cyclic olefin copolymer are preferable, because they are easy to mold and exhibit heat resistance. Incidentally, cyclic olefin polymer and cyclic olefin copolymer, which have high enough transparency to enable visual observation of the medicinal solution that is filled therein from an outside and have the heat resistance sufficient for the high pressure steam sterilization, are particularly preferable as the material to form the outer cylinder for prefilled syringe 6.

Figure 13:
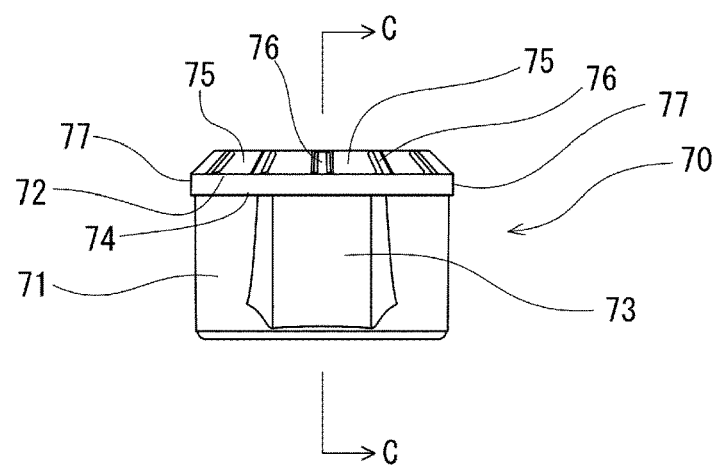
FIG. 13 is a front view of a lock adapter used in the outer cylinder for prefilled syringe that is illustrated in FIG. 6.
Figure 14:
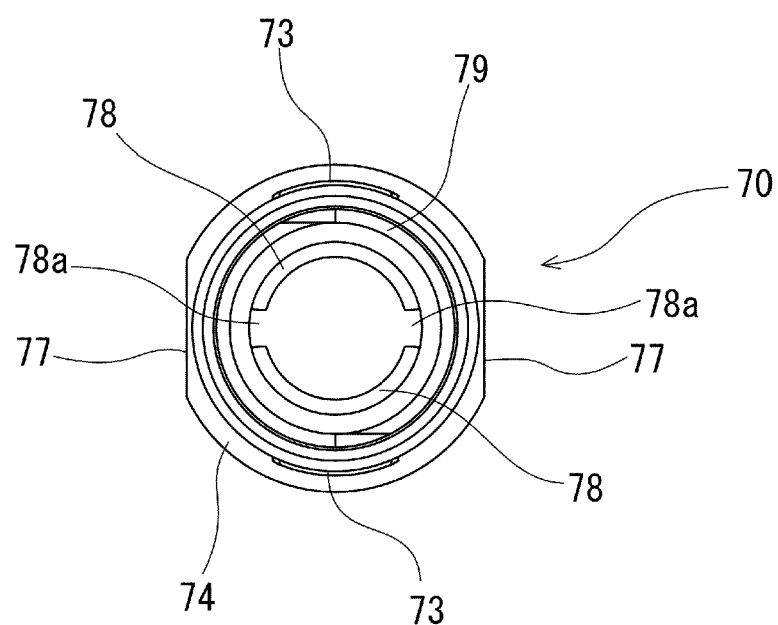
FIG. 14 is a bottom view of the lock adapter that is illustrated in FIG. 13.
Figure 15:
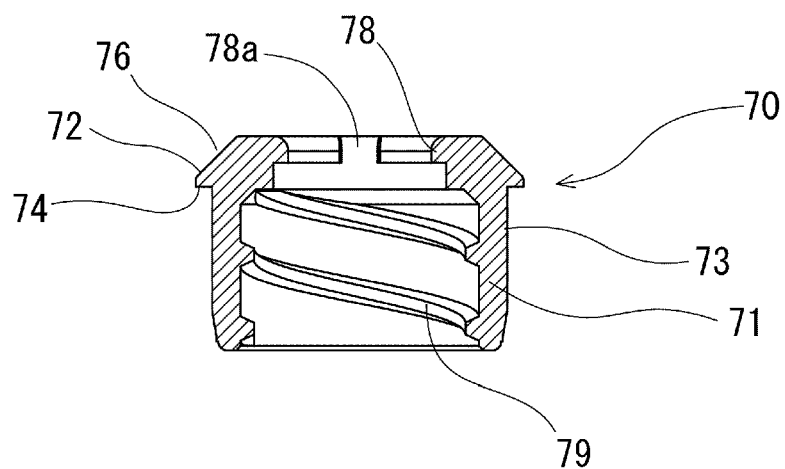
FIG. 15 is a cross-sectional view taken along a line C-C of FIG. 13.
Figure 16:
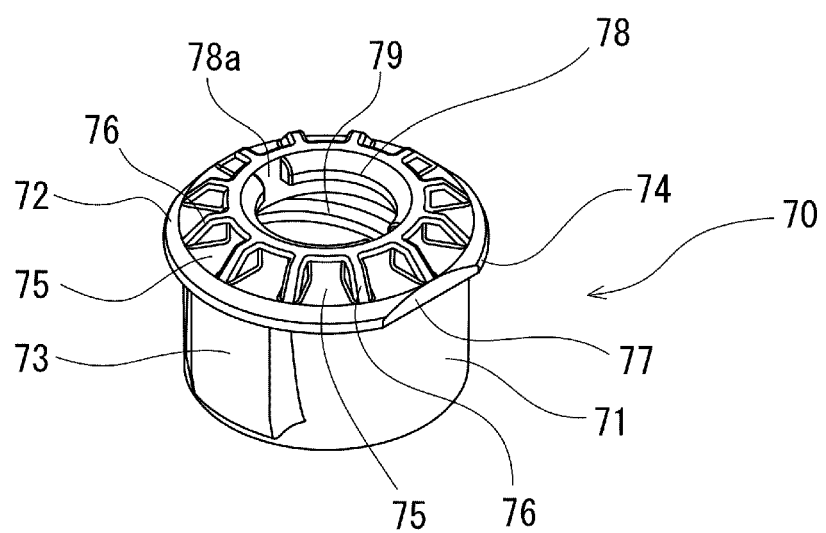
FIG. 16 is a perspective view of the lock adapter that is illustrated in FIG. 13.
Figure 17:
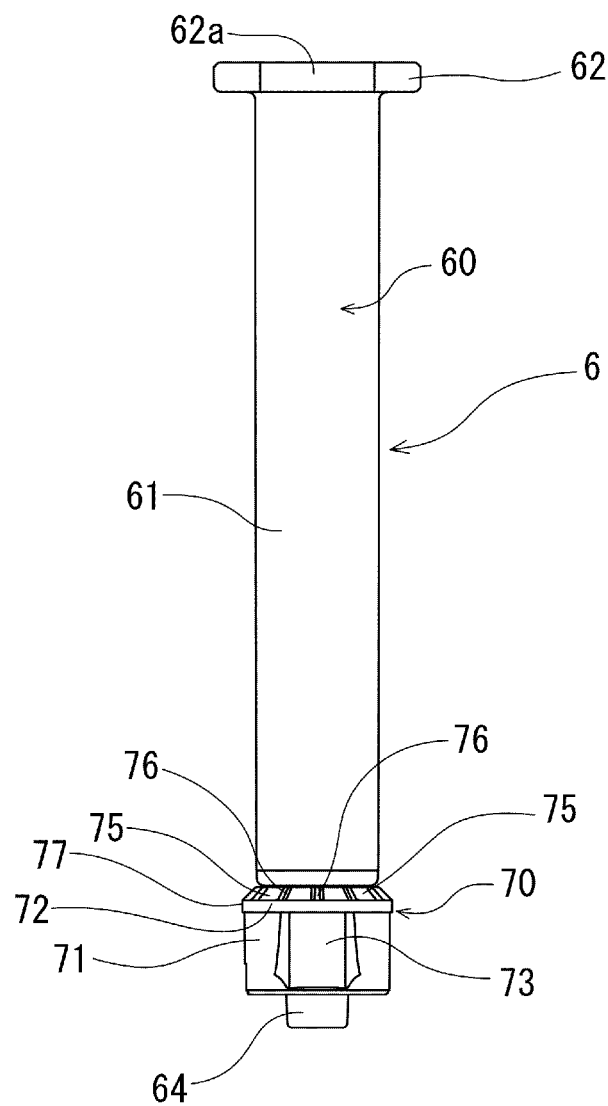
FIG. 17 is a front view of a lock adapter-attached outer cylinder main body used in the outer cylinder for prefilled syringe that is illustrated in FIG. 6.
Figure 18:
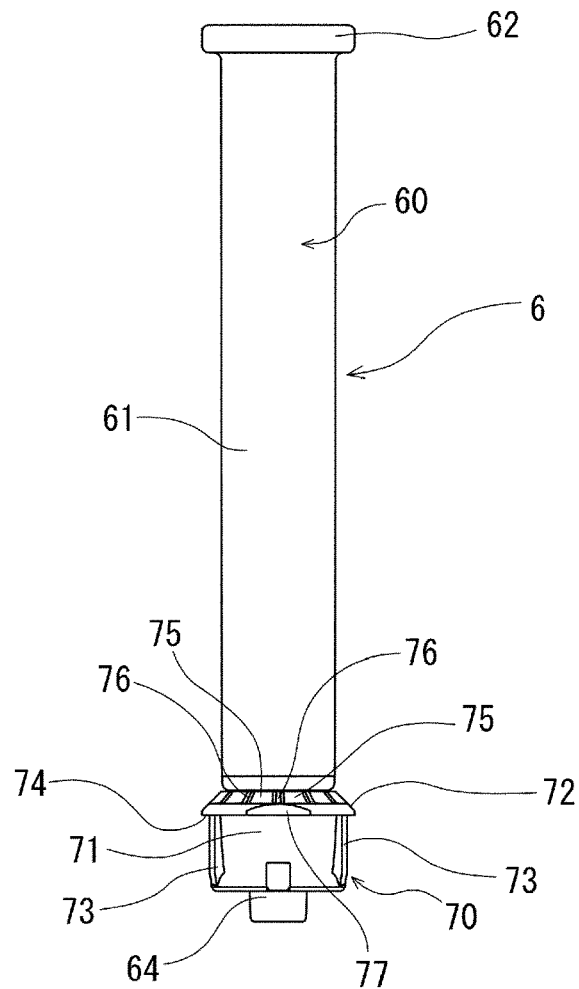
FIG. 18 is a right side view of the lock adapter-attached outer cylinder main body that is illustrated in FIG. 17.

As illustrated in FIGS. 13 and 16, the distal cylindrical part (composed of the lock adapter) of the outer cylinder for prefilled syringe 6 of this first embodiment includes: a cylindrical main body part 71; and an annular proximal part 74 that is positioned proximal of the cylindrical main body part 71. Further, the distal cylindrical part is provided with an inclined part 72. The inclined part 72 is formed of a proximal face of the annular proximal part 74, and an outer edge of a tip part of the annular proximal part 74 protrudes outward more than an outer peripheral face of the cylindrical main body part 71.

Figure 19:
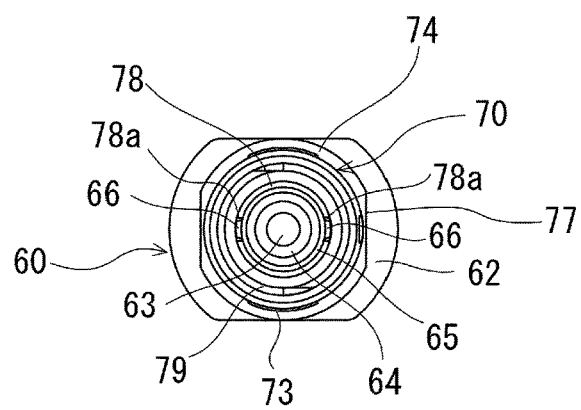
FIG. 19 is a plan view of the lock adapter-attached outer cylinder main body that is illustrated in FIG. 17.
Figure 20:
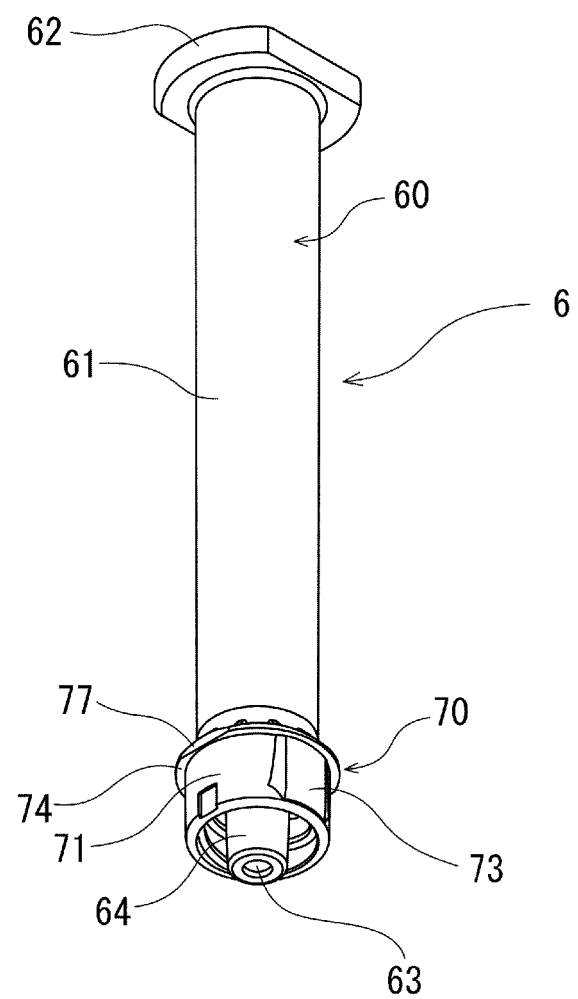
FIG. 20 is a perspective view of the lock adapter-attached outer cylinder main body that is illustrated in FIG. 17.
Figure 21:
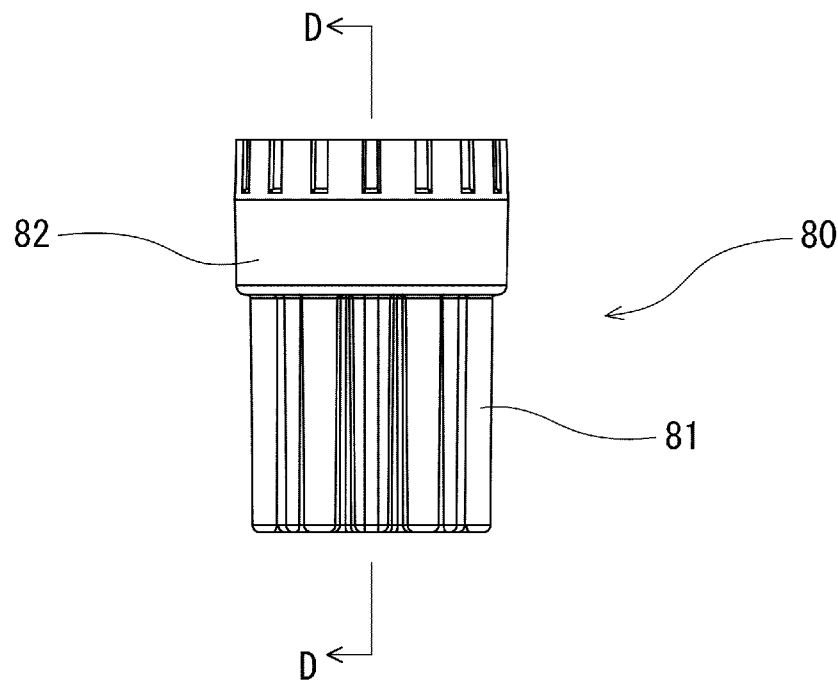
FIG. 21 is a front view of a cap used in the outer cylinder for prefilled syringe that is illustrated in FIG. 6.
Figure 22:
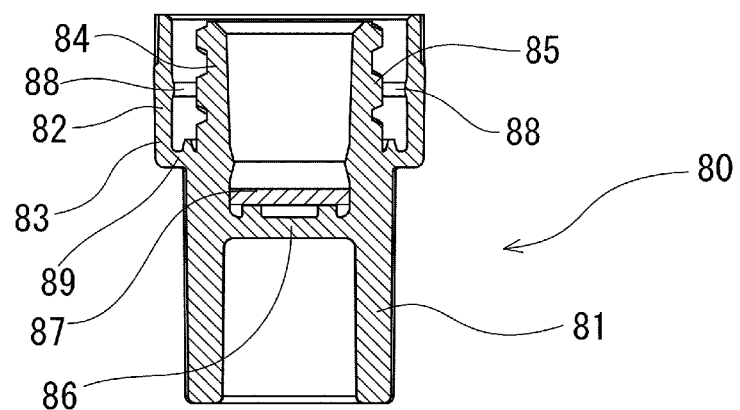
FIG. 22 is a cross-sectional view taken along a line D-D of FIG. 21.

Specifically, as illustrated in FIGS. 13 to 16, the lock adapter 70 includes: the cylindrical main body part 71; and the annular protrusion part 78 that is provided on an inner face of a proximal part of the lock adapter 70 in order to be engaged with the locking rib 65 of the outer cylinder main body 60. Incidentally, as described above, the protrusion part 78 has the notch parts 78a for storing the rotation-controlling ribs 66. When attaching the lock adapter 70 to the nozzle part 64, the annular protrusion part 78 climbs over the locking rib 65 and then enters the annular concave part 67. Thereby, the locking rib 65 of the outer cylinder main body 60 and the annular protrusion part 78 of the lock adapter 70 are engaged with each other so as to control the detachment thereof. Moreover, as illustrated in FIG. 19, the rotation-controlling ribs 66 of the outer cylinder main body 60 enter the notch parts 78a of the annular protrusion part 78 of the lock adapter 70, whereby the rotation of the lock adapter 70 is also controlled.

On an inner peripheral face of the lock adapter 70, an adapter-side screw part (a cylindrical part-side screw part) 79 that can be screwed with a below-described cap-side screw part 85 of the cap 80 is formed. In this first embodiment, the screw part 79 is formed of two helical ribs.

Further, on the proximal part of the lock adapter 70, the inclined part 72 is provided to be inclined in a proximal direction from an outer edge of the lock adapter 70 toward a position that substantially corresponds to an outer peripheral face of the outer cylinder main body part 61 of the outer cylinder for prefilled syringe 6. More specifically, the lock adapter 70 of this first embodiment has a flange part 74 (the annular proximal part) that is provided at the proximal part of the cylindrical main body part 71. The tip part of the flange part 74 protrudes outward from the cylindrical main body part 71. Moreover, the above-described inclined part 72 is formed on a proximal face of the flange part 74. Furthermore, a tip face of the flange part 74 is an erected face that crosses a central axis of the lock adapter 70 perpendicularly.

The lock adapter 70 has a maximum outer diameter part with an outer diameter that is larger than the outer diameter of the main body part 61 of the outer cylinder main body 60. Further, the outer diameter of the maximum outer diameter part of the lock adapter 70 is smaller than the inner diameter of the cylindrical part 42 of the outer cylinder holding member 4, and the lock adapter 70 can pass through the cylindrical part 42. The outer diameter of the maximum outer diameter part of the lock adapter 70 is smaller than the inner diameter of the outer cylinder holding opening part 45 (the cylindrical part 42) preferably by 0.1 mm to 5 mm, and particularly preferably by 0.3 mm to 1 mm. Incidentally, in this embodiment, the tip part of the flange part 74 is the maximum outer diameter part of the lock adapter 70.

As shown in FIGS. 13 and 16, in the lock adapter 70 of this first embodiment, the inclined part 72 is composed of: an annular inclined part that is positioned at the outer edge of the flange part 74; and proximal faces of inclined ribs 76 that are sequential to the annular inclined part. In this first embodiment, on a proximal-side outer face of the flange part 74 of the lock adapter 70, the plural inclined ribs 76 are provided. Incidentally, in this first embodiment, twelve inclined ribs 76 are provided. Further, between the inclined ribs 76, concave parts 75 are provided. The inclined part 72 is formed to be inclined in the proximal direction from the outer edge of the flange part 74 of the lock adapter 70 toward a position that substantially corresponds to an outer peripheral face of the outer cylinder main body 60. Moreover, an outer edge of the inclined part 72 (a tip of the annular inclined part) is extended outward more than the outer peripheral face of the cylindrical main body part 71 of the lock adapter 70. Thereby, when the cap 80 is attached to the lock adapter 70, the inclined part starts from a position that substantially corresponds to a proximal outer peripheral face of the cap 80.

As shown in FIGS. 17 to 20, the lock adapter 70 is attached to the outer cylinder main body 60. Further, an inclination angle of the inclined part 72 (the annular inclined face and the proximal faces of the inclined ribs 76) of the flange part 74 of the lock adapter 70 preferably ranges from 20 to 70 degrees with respect to the central axis of the outer cylinder main body part 61. The inclination angle particularly preferably ranges from 40 to 60 degrees. Moreover, the inclined ribs 76 are formed in a board shape of which a transverse cross section is rectangular, and a thickness of the inclined ribs 76 is about 1 mm. Furthermore, these inclined ribs 76 are arranged at constant intervals of about 30 degrees around the central axis of the lock adapter 70. More specifically, the interval is about 1.5 mm on the cylindrical main body part 71 side of the lock adapter 70, and is about 1 mm on the outer cylinder main body part 61 side.

Further, as shown in FIGS. 14, 16 and 18 to 20, on a lateral face of the flange part 74 of the lock adapter 70, linear parts 77 are provided so as to face each other. These facing linear parts 77 are used as marks for determining a position of the lock adapter 70 when the lock adapter 70 is attached to the outer cylinder main body 60. Moreover, the linear parts 77 can be used also as grip parts at the time of the attachment.

Figure 23:
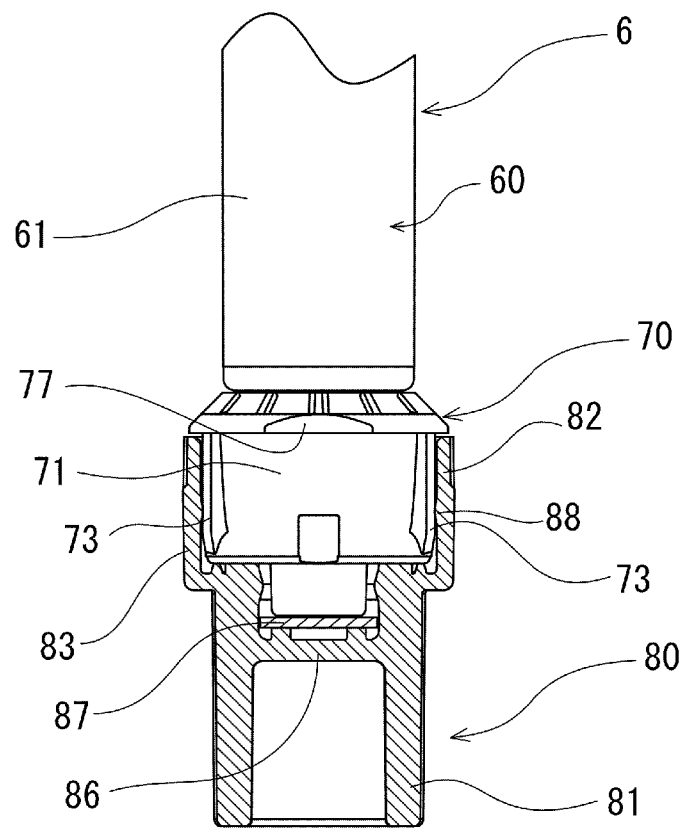
FIG. 23 is an explanatory drawing for explaining an attachment state of the cap to the lock adapter in the outer cylinder for prefilled syringe that is illustrated in FIG. 6.

Further, on the outer peripheral face of the cylindrical main body part 71 of the lock adapter 70, protrusion parts 73 are provided. In this first embodiment, the protrusion parts 73 are extended substantially parallel with a central axis of the cylindrical main body part 71. Moreover, the two protrusion parts 73 having a predetermined width are provided so as to face each other. These protrusion parts 73 contact with an inner face of a below-described rib 88 of the cap 80 as illustrated in FIG. 23, when the cap 80 is attached to the lock adapter 70, and the protrusion parts 73 and the inner face of the rib 88 press each other, thereby preventing looseness of the cap 80 that is attached to the lock adapter 70.

As shown in FIGS. 6, 7, 9 and 21 to 23, the cap 80 is formed in a cylindrical shape and includes: a tip part 81; and an attachment part 82 that is formed so that its outer diameter may be larger than that of the tip part 81 and that covers the outer peripheral face of the cylindrical main body part 71 of the lock adapter 70. The tip part 81 functions as an operation part (a grip part) for rotating the cap 80.

The attachment part 82 has a double-pipe structure that is composed of: an outside cylindrical part 83 that covers the outer peripheral face of the cylindrical main body part 71 of the lock adapter 70; and an inside cylindrical part 84 that is positioned between the lock adapter 70 and the nozzle part 64 of the outer cylinder main body 60. Further, the outside cylindrical part 83 and the inside cylindrical part 84 are connected via the connection part 89 that is provided at a tip part of the outside cylindrical part 83. Incidentally, the tip part and the attachment part may have the same outer diameters. Moreover, the tip part may be larger than the attachment part as long as the tip part can pass through the outer cylinder holding opening part 45. In this case, the cap 80 preferably has an inclined part, which is similar to the inclined part 72 at the proximal part of the lock adapter 70, between the tip part and the attachment part.

Further, an interval between an inner peripheral face of the outside cylindrical part 83 and an outer peripheral face of the inside cylindrical part 84 is set so that the cylindrical main body part 71 of the lock adapter 70 can enter therebetween. On the outer peripheral face of the inside cylindrical part 84, the cap-side screw part 85 that can be screwed with the adapter-side screw part (the cylindrical part-side screw part) 79 of the lock adapter 70 is provided. Incidentally, in this first embodiment, the connection part 89 of the cap 80 and the tip of the cylindrical main body part 71 of the lock adapter 70 are in contact with each other, whereby overtightening between the adapter-side screw part 79 and the cap-side screw part 85 is prevented.

The attachment part 82 of the cap 80 of this first embodiment has the inside cylindrical part 84 that includes the cap-side screw part 85 that can be screwed. Further, the cap 80 includes: a sealing member 87 that is stored in the inside cylindrical part 84 and that seals the tip opening part 63 of the nozzle part 64 of the outer cylinder main body 60; and the rib 88 that is formed annularly on the inner face of the outside cylindrical part 83. Incidentally, the rib 88 may be formed intermittently on substantially the same circumference.

The rib 88 of the cap 80 is formed at a position that has a distance of a predetermined length from an opening end of the cap 80 toward the sealing member 87 so as to cross a central axis of the cap 80 substantially perpendicularly. A cross section of the rib 88 is preferably semi-ellipsoid, semicircular or triangular. Further, a height of the rib 88 from the inner peripheral face of the outside cylindrical part 83 preferably ranges from 0.05 mm to 0.15 mm.

The cap 80 is attached to the tip part of the outer cylinder for prefilled syringe 6 (the outer cylinder main body 60) by the screw between the cylindrical part-side screw part (the adapter-side screw part) 79 and the cap-side screw part 85. The cap 80 prevents looseness between the rib 88 of the cap 80 and the protrusion part 73 of the distal cylindrical part (the lock adapter 70) by a contact between them in the state where the cap 80 is attached to the outer cylinder for prefilled syringe 6 (the outer cylinder main body 60). As shown in FIG. 23, because the inner face of the rib 88 of the cap 80 and an outer face of the protrusion part 73 of the distal cylindrical part (the lock adapter 70) contact with each other and are in a state of pressing each other, resistance of rotating the attached cap 80 is increased, thereby preventing the looseness of the screw which is generated due to vibration during the transportation. Moreover, because the annular rib 88 is pressed to the outside by the protrusion part 73, the inner face of the outside cylindrical part 83 of the cap 80 is deformed slightly to the outside in a part where the rib 88 and the protrusion part 73 contact with each other and is deformed slightly to the inside in a part where the rib 88 and the protrusion part 73 do not contact with each other during the high pressure steam sterilization. In the part where the inner face of the outside cylindrical part 83 is deformed slightly to the inside, the resistance due to the contact between the protrusion part 73 and the rib 88 is increased, thereby preventing the looseness of the screw that is generated due to the vibration during the transportation more securely.

Figure 25:
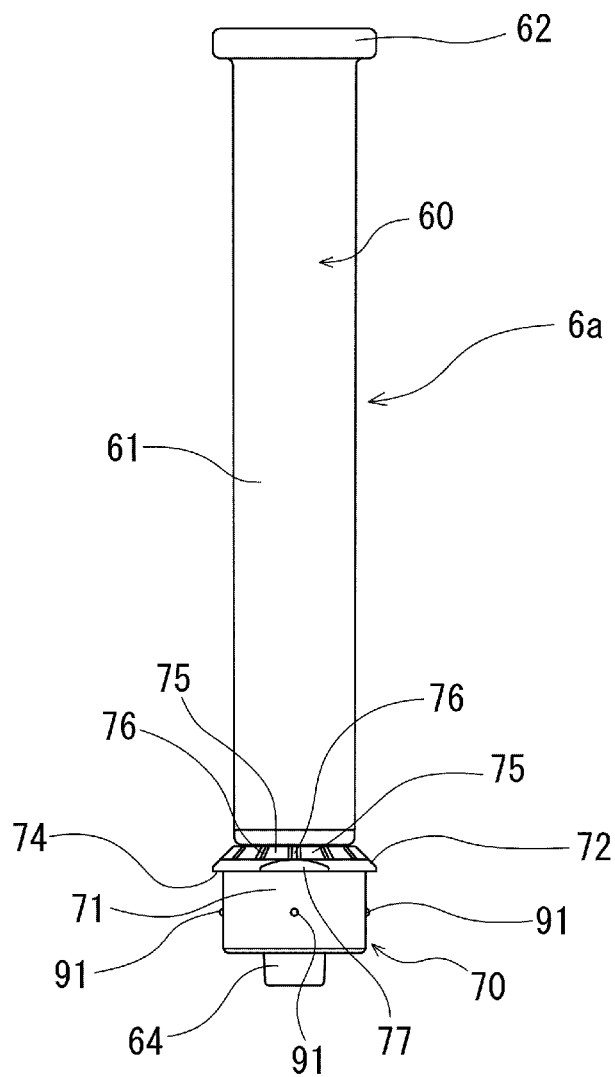
FIG. 25 is a front view of an outer cylinder for prefilled syringe of a modified example in the first embodiment of the present invention.

Incidentally, in the distal cylindrical part (the lock adapter 70), the protrusion part that is provided on the outer peripheral face of the cylindrical main body part 71 may have a shape similar to that of a protrusion 91 that an outer cylinder for prefilled syringe 6a of a modified example of the first embodiment has, as illustrated in FIG. 25.

The protrusion 91 is provided on the outer peripheral face of the cylindrical main body part 71 in a position that has a distance of a predetermined length from the tip opening toward the proximal side. The plural protrusions 91 are provided not sequentially but substantially on the same circumference. Further, the plural protrusions 91 are preferably arranged at substantially constant intervals. A height of the protrusions 91 preferably ranges from 0.05 mm to 0.15 mm. The number of the protrusions 91 preferably ranges from 2 to 6. Incidentally, the protrusions 91 may be formed in an annular shape.

Further, the rib 88 of the cap 80 is engaged with the protrusion 91 that is provided on the outer peripheral face of the cylindrical main body part 71 of the distal cylindrical part (the lock adapter 70) from the proximal side, when the cap 80 is attached to the distal cylindrical part (the lock adapter 70). Specifically, in the state where the cap 80 and the distal cylindrical part (the lock adapter 70) are screwed with each other, and the nozzle part 64 of the outer cylinder main body 6 is in contact with the sealing member 87, the rib 88 of the cap 80 climbs over the protrusion 91 of the distal cylindrical part (the lock adapter 70) from the distal so as to be in contact with the protrusion 91 from the proximal side. In this case, when rotating the attached cap 80 in a direction to detach it, there is resistance for the rib 88 to climb over the protrusion 91, thereby preventing the looseness of the screw which is generated due to the vibration during the transportation.

In this first embodiment, the cap 80 is detachably attached to the tip part of the outer cylinder main body 60 of the outer cylinder for prefilled syringe 6 via the lock adapter 70. In the state where the cap 80 is attached to the lock adapter 70, the proximal part of the outside cylindrical part 83 is positioned more closely to the tip than the inclined part of the lock adapter 70.

Further, the inside cylindrical part 84 is provided with a bottom part 86 on its distal side, and the sealing member 87 in a board shape is stored so as to contact with a protrusion part of this bottom part 86. When the cap 80 is attached to the nozzle part 64 via the lock adapter 70, the tip opening part 63 of the nozzle part 64 is sealed by the sealing member 87. Incidentally, the sealing member 87 is not limited to the board shape, and may have a cylindrical shape with a bottom part that covers the tip opening part 63 of the nozzle part 64 and a cylinder part that covers an outer peripheral face of the nozzle part 64.

As a material to form the sealing member 87, elastic materials including: natural rubber; synthetic rubber such as isoprene rubber, butyl rubber, butadiene rubber, fluororubber and silicone rubber; thermoplastic elastomer such as olefin-based elastomer and styrene-based elastomer; and the like are preferably used.

Then, the outer cylinder 6 of this first embodiment is provided with the above-described cap 80, and a maximum outer diameter part of the cap 80 can pass through the outer cylinder holding opening part 45. Specifically, an outer diameter of the maximum outer diameter part of the cap 80 is smaller than the inner diameter of the outer cylinder holding opening part 45 (the cylindrical part 42) preferably by 0.1 mm to 5 mm, and particularly preferably by 0.3 mm to 1 mm.

Examples of a material to form the lock adapter 70 and the cap 80 include various kinds of resins such as polypropylene, polyethylene, polystyrene, polyamide, polycarbonate, polyvinyl chloride, poly-(4-methyl pentene-1), an acrylic resin, acrylonitrile-butadiene-styrene copolymer, polyester such as polyethylene terephthalate and cyclic polyolefin, and among them, the resins such as polypropylene and cyclic polyolefin are preferable because they are easy to mold and exhibit heat resistance.

Next, an action of the outer cylinder packaging for prefilled syringes 1 according to the first embodiment of the present invention will be explained with reference to FIG. 24. When withdrawing the outer cylinder for prefilled syringe 6 from the outer cylinder packaging for prefilled syringes 1, the withdrawal can be carried out smoothly as described below. The outer diameter of the outer cylinder main body part 61 of the outer cylinder for prefilled syringe 6 is smaller than the cylindrical main body part 71 of the lock adapter 70 and is smaller than the inner diameter of the cylindrical part 42 of the outer cylinder holding member 4. Thus, as shown by the outer cylinder for prefilled syringe 6 in right end of FIG. 24, the outer cylinder main body part 61 is sometimes withdrawn upward in a state of being eccentric with respect to the cylindrical part 42. In such a case, the inclined part 72 (specifically, an upper face of the rib 76) is in contact with the opening 45b at the lower end of the outer cylinder holding opening part 45; however, because an upper face of the inclined part 72 (the inclined rib 76) is inclined, the lock adapter 70 is not caught by the opening 45b, and the outer cylinder for prefilled syringe 6 is guided so that a central axis of the outer cylinder for prefilled syringe 6 may approach a central axis of the cylindrical part 42, as shown by the outer cylinder for prefilled syringe 6 in middle of FIG. 24.

Because the plural inclined ribs 76 are formed along an outer periphery of the lock adapter 70 so that intervals between the inclined ribs 76 may not be longer than a predetermined length, the inclined ribs 76 are structured so that the inclined ribs 76 can be in contact with whole circumference of the lock adapter 70, and the above-described guidance can be carried out in whichever direction the outer cylinder for prefilled syringe 6 is eccentric. Further, in this first embodiment, because the annular inclined face 46 is provided also on the opening 45b side that is at the lower end of the outer cylinder holding opening part 45, the outer cylinder for prefilled syringe 6 can be guided more smoothly.

Figure 26:
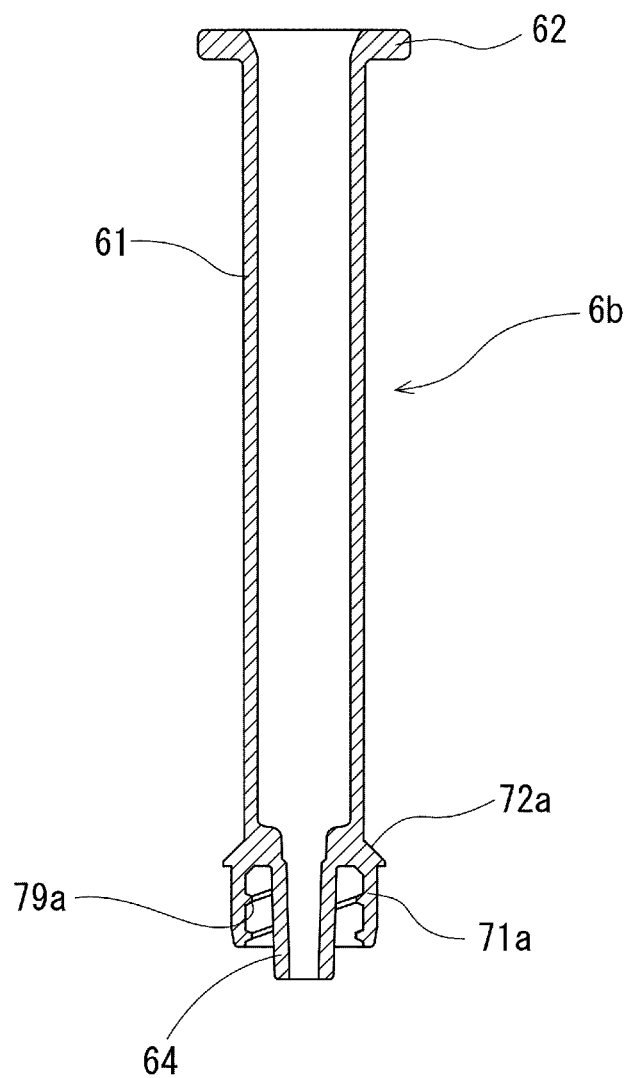
FIG. 26 is a longitudinal cross-sectional view of an outer cylinder for prefilled syringe of a second embodiment of the present invention.
Figure 27:
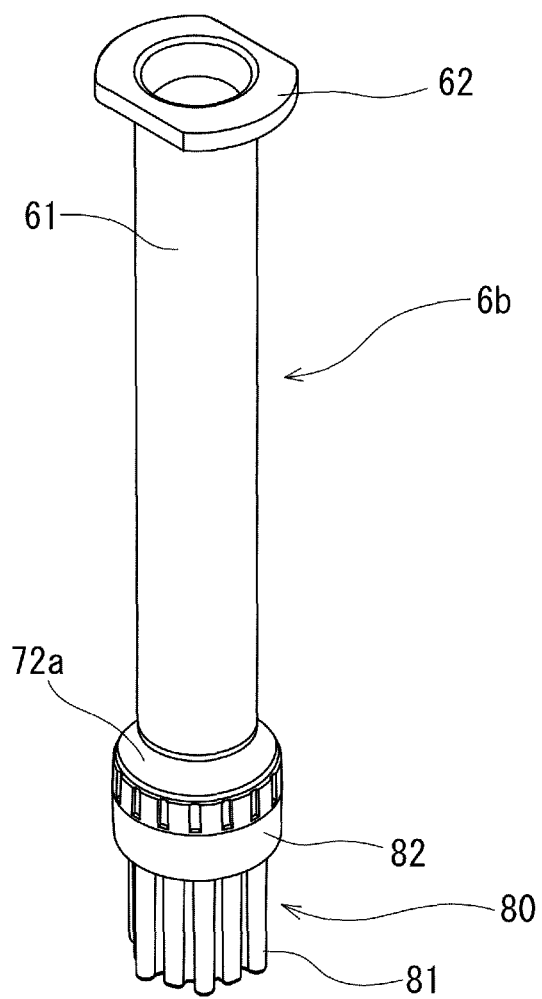
FIG. 27 is a perspective view of the outer cylinder for prefilled syringe that is illustrated in FIG. 26.

Moreover, the outer cylinder for prefilled syringe of the present invention may also be an outer cylinder for prefilled syringe 6b of a second embodiment as illustrated in FIGS. 26 and 27. Distinction of this outer cylinder for prefilled syringe 6b of the second embodiment from the above-described outer cylinder for prefilled syringe 6 of the first embodiment is a distal cylindrical part 71a and an inclined part 72a. Therefore, with regard to the constituents except these members, the explanation of the outer cylinder for prefilled syringe 6 will be referred to.

As shown in FIG. 26, in the outer cylinder for prefilled syringe 6b, the constituent that corresponds to the lock adapter 70 of the first embodiment is formed integrally with the outer cylinder main body part 61 so as to constitute the distal cylindrical part 71a. On an inner peripheral face of the distal cylindrical part 71a, a cylindrical part-side screw part 79a is formed. As illustrated in FIG. 27, also in the second embodiment, the cap 80 is detachably attached to a tip part of the outer cylinder for prefilled syringe 6b. The inclined part 72a is not provided with an inclined face for each of the plurality of ribs. The inclined part 72a is structured with an annular inclined face that is formed on the proximal part of the distal cylindrical part 71a. Thus, a whole of the inclined part 72a is in contact with the opening 45b at the lower end of the outer cylinder holding opening part 45 so as to be able to guide the outer cylinder for prefilled syringe 6b. Incidentally, also in the above-described outer cylinder for prefilled syringe 6, the inclined part may be formed by allowing the proximal part of the distal cylindrical part (a distal cylindrical member) to be an annular inclined face as the outer cylinder for prefilled syringe 6b described above.

The "inclined part" of the embodiments of the present invention may be provided with a unit that is inclined, which is not limited to the rib, as represented by the above-described two embodiments. This inclined unit is not limited to the flat face, and may be structured with a curved face. Further, in the first embodiment, the number, a width, intervals and the like of the inclined ribs 76 are not limited to the above-described numbers, as long as the outer cylinder for prefilled syringe 6 is structured so that the inclined ribs 76 may be in contact with the opening 45b at the lower end of the outer cylinder holding opening part 45 so as to guide the outer cylinder for prefilled syringe 6. Moreover, the example of the outer cylinder packaging for prefilled syringes 1, in which the cylindrical part 42 of the outer cylinder holding member 4 is provided with the outer cylinder holding opening part 45 in order to hold the outer cylinder for prefilled syringe 6 stably, was provided, but the present invention is not limited to this example, and can be applied also to an outer cylinder packaging for prefilled syringes in which the substrate part 41 is provided directly with the outer cylinder holding opening part, for example.

Also, the outer cylinder for prefilled syringe of the present invention may be in the form of a third embodiment which is illustrated in FIGS. 28 to 32. Incidentally, an outer cylinder for prefilled syringe 6c of this third embodiment is also provided with the inclined part 72. As shown in FIGS. 28 to 31, a cap 80a is attached to a tip part of an outer cylinder main body 60c. Then, the cap 80a can be opened by rotating an operation part 182 of the cap 80a (see FIG. 32).

Distinction of this outer cylinder for prefilled syringe 6c of the third embodiment from the above-described outer cylinder for prefilled syringe 6 is structural differences in their lock adapters and caps. Incidentally, in this outer cylinder for prefilled syringe 6c of the third embodiment, the lock adapter 70a is provided with the inclined part 72 as in the outer cylinder for prefilled syringe 6 of the above-described two embodiments.

Figure 28:
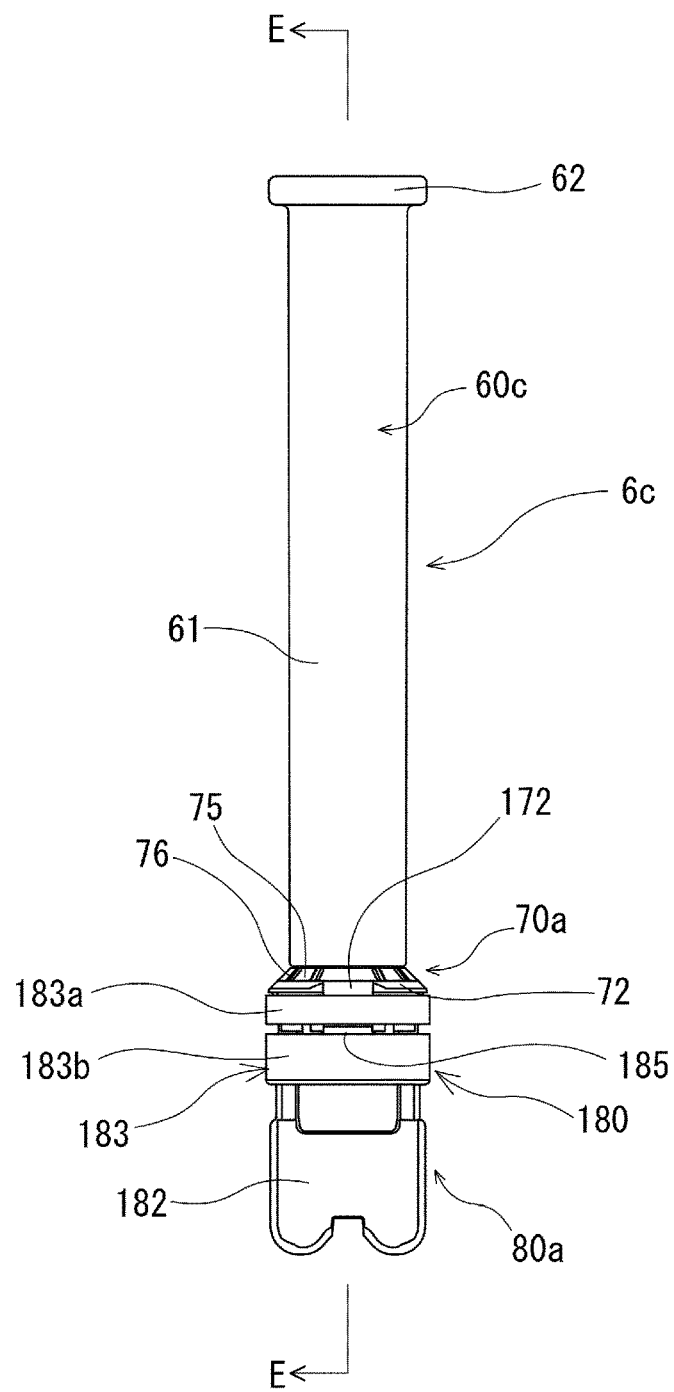
FIG. 28 is a front view of an outer cylinder for prefilled syringe of a third embodiment of the present invention.
Figure 29:
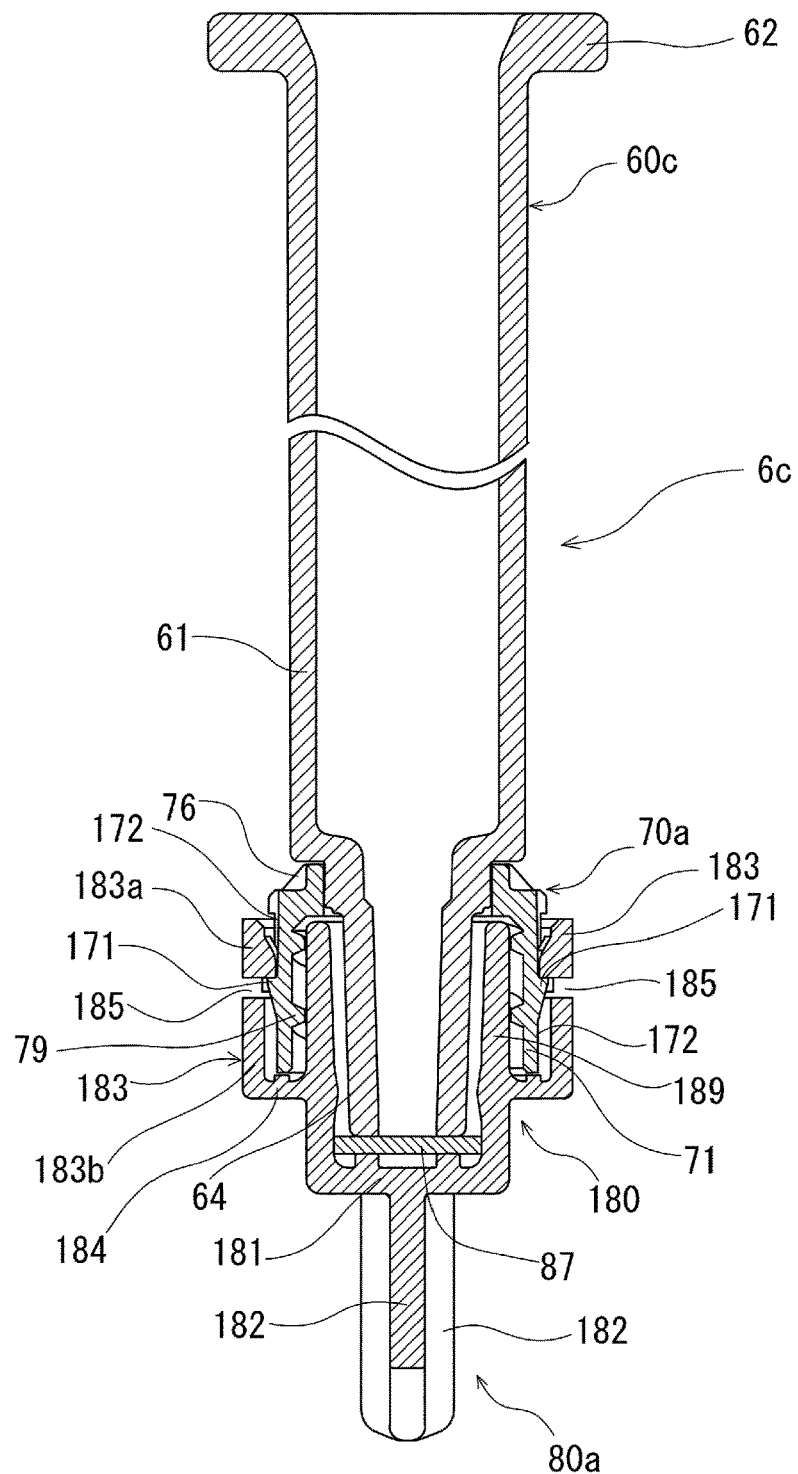
FIG. 29 is a partially-omitted enlarged cross-sectional view that is taken along a line E-E of FIG. 28.
Figure 30:
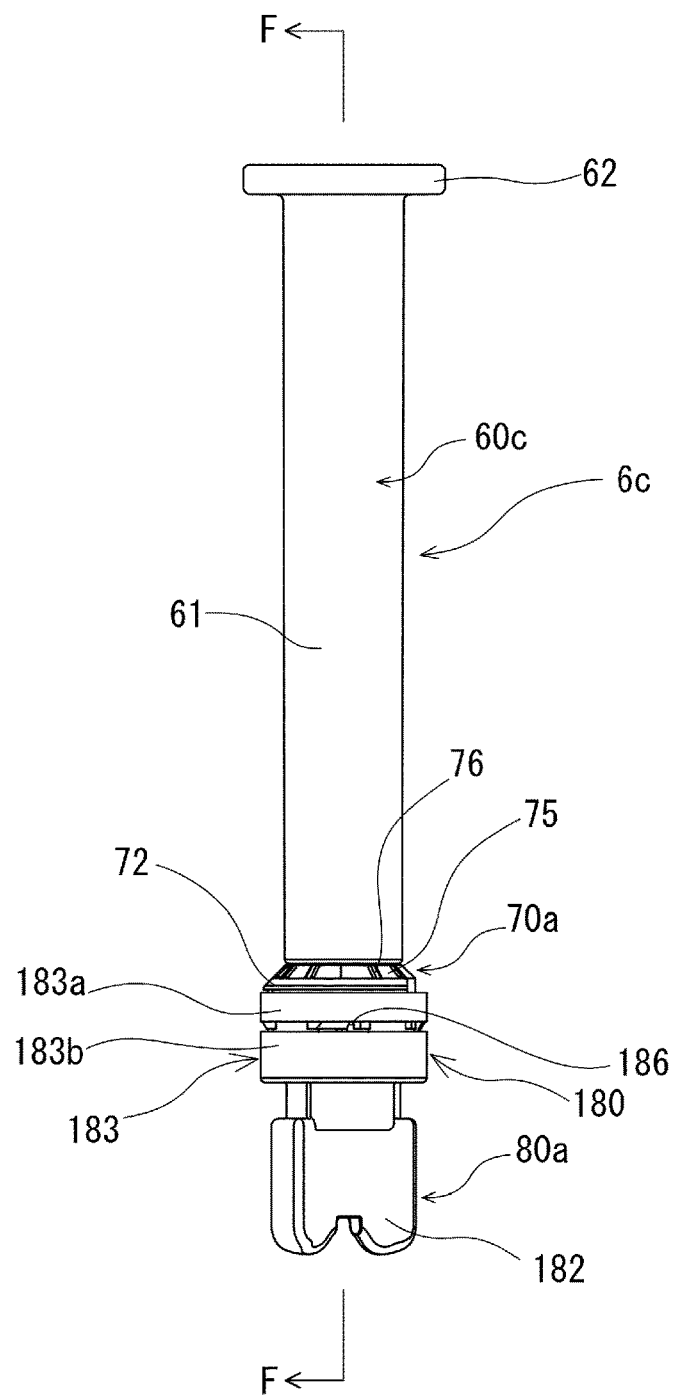
FIG. 30 is a view illustrating a state where the outer cylinder for prefilled syringe of FIG. 28 is rotated around a central axis by 40 degrees.
Figure 31:
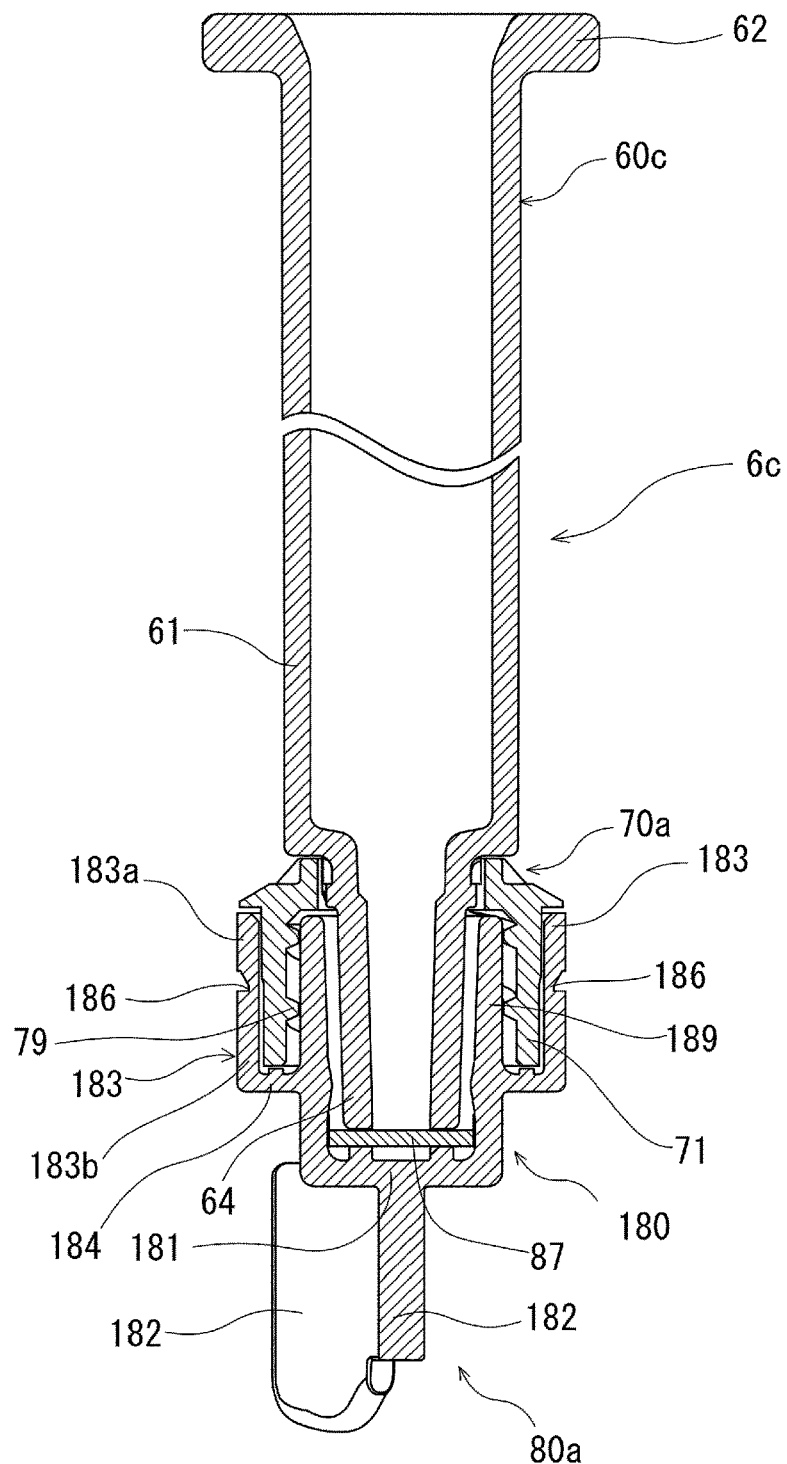
FIG. 31 is a partially-omitted enlarged cross-sectional view that is taken along a line F-F of FIG. 30.
Figure 33:
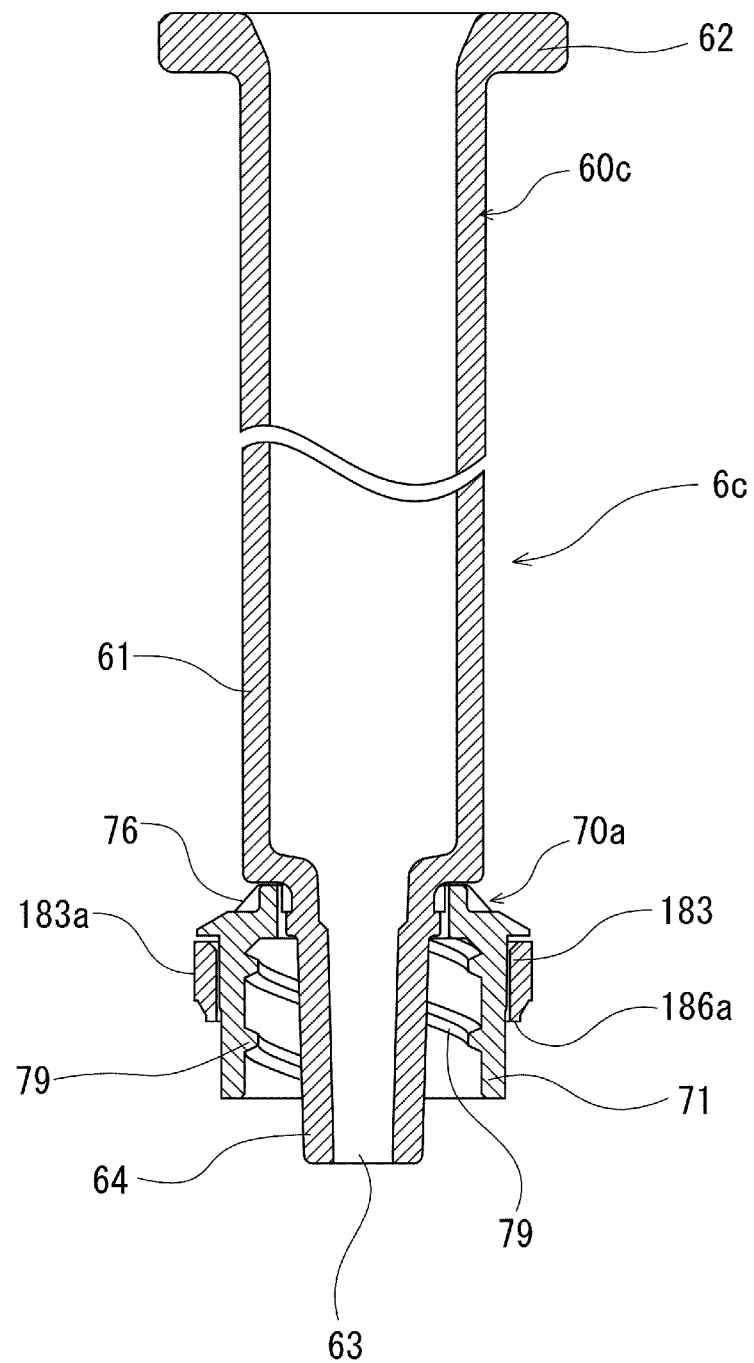
FIG. 33 is an explanatory drawing for explaining an action of the outer cylinder for prefilled syringe that is illustrated in FIG. 28.

FIG. 28 is a front view of the outer cylinder for prefilled syringe of the third embodiment of the present invention. FIG. 29 is a partially-omitted enlarged cross-sectional view taken along a line E-E of FIG. 28. FIG. 30 is a view illustrating a state where the outer cylinder for prefilled syringe of FIG. 28 is rotated around a central axis by 40 degrees. FIG. 31 is a partially-omitted enlarged cross-sectional view taken along a line F-F of FIG. 30. FIG. 32 is an explanatory drawing for explaining constituent members of the outer cylinder for prefilled syringe that is illustrated in FIG. 28. FIG. 33 is an explanatory drawing for explaining an action of the outer cylinder for prefilled syringe that is illustrated in FIG. 28.

In this third embodiment, the outer cylinder for prefilled syringe 6c includes: an outer cylinder main body 60c; the lock adapter 70a that covers the nozzle part 64; and the cap 80a.

The cap 80a includes: an attachment part 180 that covers the outer peripheral face of the cylindrical main body 71 of the lock adapter 70a; and a tip part 182 that is provided at a tip of the attachment part 180 and functions as the operation part to be gripped for a breaking operation. As shown in FIG. 31, the attachment part 180 is formed in cylindrical shape and has a double-pipe structure that is composed of: an outside cylindrical part 183 that covers the outer peripheral face of the cylindrical main body 71 of the lock adapter 70a; and an inside cylindrical part 189 that is positioned between the lock adapter 70a and the nozzle part 64 of the outer cylinder main body 60c. The outside cylindrical part 183 includes: a lateral opening part 185 that is formed near a central part in a central axis direction of the outside cylindrical part 183; a proximal ring part 183a that is positioned on a proximal side of the lateral opening part 185; a tip ring part 183b that is positioned on a distal of the lateral opening part 185; and a breakable part (a breakable connection part) 186 that is positioned in the lateral opening part 185 and connects the proximal ring part 183a and the tip ring part 183b. Further, the outside cylindrical part 183 and the inside cylindrical part 189 are connected by a connection part 184 that is provided at a tip part of the outside cylindrical part 183. By rotating the tip part 182 around the central axis of the cap 80, the outside cylindrical part 183 (the cap 80a) is broken in the breakable part 186 and separated. Incidentally, by the break of the breakable part 186, the proximal ring part 183a of the outside cylindrical part 183 remains on the lock adapter 70a side, and the other units of the cap 80a are detached from the outer cylinder main body 60c (the lock adapter 70a).

As illustrated in FIGS. 28 to 32, the lock adapter 70a has a cylindrical shape and is disposed concentrically in an outer peripheral part of the nozzle part 64 of the outer cylinder. This lock adapter 70a fixes a medical instrument that is to be connected to the nozzle part 64. Moreover, as in the above-described two embodiments, the detachment from the outer cylinder main body 60c and rotation around the axis of the lock adapter 70a is controlled. In this third embodiment, as shown in FIG. 32, the plural protrusion parts 78 that are formed to protrude toward a proximal inner peripheral part of the lock adapter 70a and the ribs 66 that are formed at a proximal of the outer peripheral part of the nozzle part 64 of the outer cylinder main body 60c are engaged with each other so as to control the rotation of the lock adapter 70a. Moreover, a mountain part of the protrusion part 78 of the lock adapter 70a enters the concave part 67 that is formed between the ribs 66 of the nozzle part 64 and is engaged with the locking rib 65, thereby controlling the detachment of the lock adapter 70a from the outer cylinder.

Further, the lock adapter 70a and the cap 80a have engagement mechanisms. The engagement mechanism of the cap 80a is provided on the outside cylindrical part 183 of the attachment part 180. An outer peripheral part of the lock adapter 70a includes a groove part 172 that extends along an axis direction of the lock adapter 70a and has a predetermined width. The two groove parts 172 are provided so as to face each other. Further, in a middle of the groove part 172, an engagement rib 171 is provided so as to traverse the groove part 172. The engagement rib 171 has: a distal face that is inclined toward the central axis of the lock adapter 70a; and a proximal-side face that is substantially perpendicular to the central axis of the lock adapter 70a.

The cap 80a has a protrusion part 188 that is provided on an inner face of the proximal ring part 183a of the outside cylindrical part 183 of the attachment part 180 and is engaged with the engagement rib 171 of the lock adapter 70a. When pressing the cap 80a from the distal side to the outer cylinder main body 60c for attaching the cap 80a to the outer cylinder main body 60c, the protrusion part 188 that is provided on the inner face of the proximal ring part 183a of the cap 80a is firstly inserted into a distal side of the groove part 172, then is moved along a distal inclined face of the engagement rib 171, and further climbs over a top part of the engagement rib 171, so that the engagement rib 171 and the protrusion part 188 become engaged with each other. Then, by the engagement between the engagement rib 171 and the protrusion part 188, the detachment of the cap 80a from the outer cylinder main body 60c (the lock adapter 70a) can be controlled. Further, the groove part 172 and the protrusion part 188 are engaged with each other, whereby the rotation of the cap 80a with respect to the outer cylinder main body 60c (the lock adapter 70a) can be controlled. Moreover, on a proximal side of the outer peripheral part of the lock adapter 70a, two protrusions 174 are formed. These protrusions 174 are stored in concave parts 187 that are formed on the inner face of the proximal ring part 183a of the outside cylindrical part 183 of the cap 80a. Then, the protrusion 174 and the concave part 187 are engaged with each other, so that the rotation of the cap 80a with respect to the outer cylinder main body 60c (the lock adapter 70a) is controlled more and rotation of the proximal ring part 183a, which remains on the lock adapter 70a side after the break of the breakable part 186 of the cap 80a, with respect to the lock adapter 70a is also controlled.

As described above, the proximal ring part 183a of the cap 80a is connected with the tip ring part 183b by the breakable part 186 (see FIG. 31). Further, the cap 80a includes: the sealing member 87 that is stored in the inside cylindrical part 189 of the attachment part 180 and that seals the tip opening part 63 of the nozzle part 64 of the outer cylinder main body 60c; and the tip part 182 that protrudes from the attachment part 180 in the distal direction. The sealing member 87 seals the tip opening part 63 of the nozzle part 64 of the outer cylinder main body 60c liquid-tightly. The tip part 182 is a part to be gripped for rotating the cap 80a so as to open the cap 80a. As illustrated in FIGS. 28 to 31, the tip part 182 is formed in a plate shape (flat shape) so that it can be gripped easily.

The attachment part 180 is provided with the above-described proximal ring part 183a on its proximal side. The proximal ring part 183a is attached to the proximal part of the outer peripheral part of the lock adapter 70a. The proximal ring part 183a is connected with the tip ring part 183b by the breakable part 186. Then, by the opening operation, that is, by gripping the outer cylinder main body 60c and rotating the tip part 182 around the axis, the breakable part 186 exceeds a breaking limit to be broken. By this break, the proximal ring part 183a is separated from the attachment part 180, and the cap 80a is detached from the outer cylinder main body 60c, and further, a broken part 186a is formed in the proximal ring part 183a by the break of the breakable part 186, as shown in FIG. 33.

The breakable part 186 is composed of plural fragile parts (specifically, thin wall parts) that are disposed intermittently around the axis of the cap 80a (the proximal ring part 183a). Thereby, the breakable part 186 is a part that can be broken easily during the opening operation. Incidentally, the number of the fragile parts to be disposed is determined according to a size and a kind of the material to form the cap 80a, and for example, it preferably ranges from 2 to 8, and more preferably ranges from 4 to 6. Also, a thickness of each of the fragile parts is determined according to the size and the kind of the material to form the cap 80a, and for example, it preferably ranges from 0.1 mm to 2.0 mm, and more preferably ranges from 0.2 mm to 0.6 mm.

Moreover, as described above, the attachment part 180 is provided with the inside cylindrical part 189 that is positioned between the lock adapter 70a and the nozzle part 64 of the outer cylinder main body 60c. The inside cylindrical part 189 is positioned inside the outside cylindrical part 183 that has a cylindrical shape and is formed concentrically with the outside cylindrical part 183. The inside cylindrical part 189 is positioned in a freely-fitting state between the nozzle part 64 of the outer cylinder main body 60c and the lock adapter 70a. Further, the lock adapter 70a and the tip ring part 183b of the outside cylindrical part 183 of the cap 80a are also in the freely-fitting state. Herein, the "freely-fitting state" means a contactless state or a contacting state which is line contact or point contact, even if both subjects contact with each other.

Because the cap 80a, the outer cylinder main body 60c and the lock adapter 70a are in the freely-fitting state as described above, when external force is applied to the tip part 182 of the cap 80a, for example, while carrying the syringe or the like, and a whole of the attachment part 180 is about to be inclined with respect to the axis of the outer cylinder main body 60c, the inside cylindrical part 189 becomes in contact with the outer peripheral part of the nozzle part 64 and the inner peripheral part of the lock adapter 70a, and the tip ring part 183b of the outside cylindrical part 183 becomes in contact with the outer peripheral part of the lock adapter 70a. Thereby, unnecessary inclination of the attachment part 180 with respect to the axis of the outer cylinder main body 60c can be prevented. Further, by such prevention of the inclination of the attachment part 180, an unintentional break of the breakable part 186 can be prevented.

The inside cylindrical part 189 is preferably formed to be extended closely to the proximal part of the lock adapter 70a. Thereby, only by slightly inclining the whole of the attachment part 180 with respect to the axis of the outer cylinder main body 60c, a proximal part of the inside cylindrical part 189 becomes in contact with the outer peripheral part of the nozzle part 64 and the inner peripheral part of the lock adapter 70a. Thus, an allowable range of the unnecessary inclination of the attachment part 180 can be decreased to the least possible, so that the unintentional break of the breakable part 186 can be prevented more securely.

An inner diameter $\phi d1$ and an outer diameter $\phi d2$ of the inside cylindrical part 189 are increased gradually toward the proximal direction correspondingly to a shape of the nozzle part 64, whereby a thickness t1 of the inside cylindrical part 189 is made substantially constant along the axis direction of the nozzle part 64. Due to such a substantially constant thickness $t1=(\phi d2-\phi d1)/2$ of the inside cylindrical part 189, a strength of the inside cylindrical part 189 can be enhanced sufficiently, so that an effect that can regulate the allowable range of the inclination of the attachment part 180 with respect to the axis of the outer cylinder main body 60c can be exerted more securely.

Further, a distance between the inside cylindrical part 189 and the nozzle part 64 in a diameter direction is preferably set to be longer than a distance between the inside cylindrical part 189 and the lock adapter 70a in the diameter direction. Thereby, when the whole of the attachment part 180 is about to be inclined with respect to the axis of the outer cylinder main body 60c, the inside cylindrical part 189 becomes in contact with the inner peripheral part of the lock adapter 70a before contacting with the outer peripheral part of the nozzle part 64. Thus, the contact between the inside cylindrical part 189 and the outer peripheral part of the nozzle part 64 can be prevented, whereby the outer peripheral part of the nozzle part 64 is prevented from being damaged.

Moreover, the inside cylindrical part 189 is provided with a bottom part 181 on its distal, and the sealing member 87 in a board shape is stored so as to contact with a protrusion part of this bottom part 181. When the cap 80a is attached to the nozzle part 64 via the lock adapter 70a, the tip opening part 63 of the nozzle part 64 is sealed by the sealing member 87.

Next, operational processes from the attached state of the cap 80a to rotating and opening of the cap 80a will be described by way of FIGS. 28 to 33.

As illustrated in FIGS. 28 to 31, the cap 80a is attached to the outer cylinder main body 60c (the nozzle part 64), and liquid-tightly seals the tip opening part 63 of the nozzle part 64 by the sealing member 87. Moreover, in this state, each of the protrusion parts 188 of the proximal ring part 183a of the cap 80a is positioned on a proximal side of the groove part 172 of the lock adapter 70a. Thereby, the rotation of the cap 80a around the axis with respect to the lock adapter 70a is prevented. Further, each of the protrusion parts 78 of the lock adapter 70a enters the concave part 67 of the outer cylinder main body 60c. Thereby, the rotation of the lock adapter 70a around the axis of the outer cylinder main body 60c is prevented. As described above, the rotation of the cap 80a around the axis of the outer cylinder main body 60c is prevented.

Further, the outer cylinder main body 60c is gripped by one hand and the tip part 182 of the cap 80a is gripped by the other hand, and the outer cylinder main body 60c and the tip part 182 of the cap 80a are rotated around the axis of the outer cylinder main body 60c respectively in directions that are opposite to each other. Thereby, the breakable part 186 is twisted to be broken (see FIG. 33). Thereby, the proximal ring part 183a is separated from the cap 80a (the attachment part 180), and the cap 80a except the proximal ring part 183a is detached from the outer cylinder main body 60c (the lock adapter 70a). Then, further thereby, the screw part of the lock adapter 70a is exposed, so that the medical part can be connected thereto. Moreover, because the proximal ring part 183a and the tip ring part 183b of the outside cylindrical part 183 are connected with each other via the breakable part 186, once the breakable part 186 is broken, the proximal ring part 183a and the tip ring part 183b cannot be reconnected. Furthermore, the cap 80a is attached to the outer cylinder main body 60c (the lock adapter 70a) only via the proximal ring part 183a. Thus, even if one tries to attach the cap 80a to the outer cylinder main body 60c (the lock adapter 70a) after breaking the breakable part 186 and separating the proximal ring part 183a from the cap 80a, the cap 80a cannot be reattached (recapped).

Incidentally, the outer cylinder for prefilled syringe of the present invention may be different from those of the above-described respective embodiments, and the inside cylindrical part may be omitted from the attachment part. In this case, the sealing member is held at the tip part of the cap. Further, the outside cylindrical part of the attachment part is connected with the tip part of the cap. Moreover, the attachment of the cap to the tip part of the outer cylinder main body can be achieved by, for example, the engagement mechanism between the outside cylindrical part and the lock adapter as in the third embodiment. Furthermore, in the case where the sealing member has the cylindrical shape with the bottom part that covers the opening of the nozzle part and the cylinder part that covers the outer periphery of the nozzle part and is fit with the nozzle part, the attachment of the cap to the tip part of the outer cylinder main body may also be achieved by the fit of the sealing member with the nozzle part.

Further, the outer cylinder for prefilled syringe of the present invention may be different from those of the above-described respective embodiments, and the outside cylindrical part may be omitted. In this case, the flange part may be omitted from the lock adapter (the distal cylindrical part) so that the outer edge of the inclined part may coincide with the outer edge of the cylindrical main body part of the lock adapter. Moreover, the shape of the sealing member may be different from the board shape, and may be a cylindrical shape with the bottom part that covers the opening of the nozzle part and the cylinder part that covers the outer periphery of the nozzle part. In the case where the cylinder part of the sealing member is fit with the nozzle part, the inside cylindrical part may be further omitted, that is, the attachment part itself may be omitted. In the case of omitting the attachment part, the cap is attached to the tip part of the outer cylinder main body by the sealing member. Moreover, in this case, the sealing member is held at the tip part of the cap, or is formed integrally with the tip part of the cap.

Further, the distal cylindrical part is not limited to the lock adapter as described above in the respective embodiments. The distal cylindrical part may be, for example, a needle hub having an injection needle that is attached to the nozzle part of the outer cylinder main body, or may be a needle cover for covering the injection needle that is attached to this needle hub. Incidentally, in this case, the nozzle part may have an outer diameter that is substantially equal to that of the outer cylinder main body part. Further, in the case where the injection needle is attached to the nozzle part of the outer cylinder main body part, the distal cylindrical part may be the needle cover for covering the injection needle.

According to one embodiment of the present invention, an outer cylinder packaging for prefilled syringes which stores plural outer cylinders for prefilled syringes and is sterilizable or sterilized includes: a container of which an upper face has an opening and which has a shape retainable property; an outer cylinder holding member that is stored in the container and has many outer cylinder holding opening parts; the plural outer cylinders for prefilled syringes that are held by the outer cylinder holding member; and a sheet-shaped lid member that seals the upper face opening of the container and can be peeled off. The outer cylinder for prefilled syringe includes: an outer cylinder main body part; a flange part that is provided at a proximal part of the outer cylinder main body part, protrudes outward, and cannot pass through the outer cylinder holding opening part; a nozzle part that is provided at a tip part of the outer cylinder main body part and has a tip opening part at its tip; and a distal cylindrical part which covers the nozzle part, has a diameter that is larger than an outer diameter of the outer cylinder main body part, and can pass through the outer cylinder holding opening part. The outer cylinder for prefilled syringe is inserted from a distal into the outer cylinder holding opening part of the outer cylinder holding member and is in a state where the flange part is in contact with and suspended by a rim of the outer cylinder holding opening part, and further, the outer cylinder for prefilled syringe has an inclined part which is positioned at a proximal part of the distal cylindrical part and is inclined in a proximal direction from an outer edge of the distal cylindrical part toward an outer peripheral face of the outer cylinder main body part so as to guide the outer cylinder for prefilled syringe to be withdrawn from the outer cylinder holding opening part.

In the above-described outer cylinder packaging for prefilled syringes, the outer cylinder for prefilled syringe can be guided by the inclined part, whereby the risk that the distal cylindrical part is caught by the outer cylinder holding opening part during the withdrawal of the outer cylinder for prefilled syringe can be reduced, so that the withdrawal operation can be carried out smoothly.

Further, embodiments of the above-described outer cylinder packaging for prefilled syringes may also be as follows:

In one aspect, the outer cylinder for prefilled syringe further includes a cap that is attached to a tip part of the outer cylinder for prefilled syringe and seals an opening of the nozzle part, another medical instrument can be connected to the nozzle part, the distal cylindrical part includes, on its inner peripheral face, a cylindrical part-side screw part that can be screwed with the medical instrument that is to be connected to the nozzle part, and the cap can pass through the outer cylinder holding opening part.

In one aspect, the distal cylindrical part includes: a cylindrical main body part; and an annular proximal part that is positioned at a proximal of the cylindrical main body part. The inclined part is formed of a proximal face of the annular proximal part, an outer edge of a tip part of the annular proximal part protrudes outward more than an outer peripheral face of the cylindrical main body part, and the cap includes an attachment part that covers the outer peripheral face of the cylindrical main body part.

In one aspect, the attachment part of the cap includes: an outside cylindrical part that covers the outer peripheral face of the cylindrical main body part; and an inside cylindrical part which is positioned inside the outside cylindrical part and has a cap-side screw part that can be screwed with the cylindrical part-side screw part. The cap includes: a sealing member that is stored in the inside cylindrical part and seals the opening of the nozzle part; and a rib that is formed on an inner face of the outside cylindrical part. The cap is attached to the tip part of the outer cylinder for prefilled syringe by screwing between the cylindrical part-side screw part and the cap-side screw part, the distal cylindrical part includes a protrusion part that is provided on the outer peripheral face of the cylindrical main body part, and the cap prevents looseness between the rib and the protrusion part by a contact between the rib and the protrusion part in a state where the cap is attached to the outer cylinder for prefilled syringe.

In one aspect, in the outer cylinder for prefilled syringe in the state where the cap is attached, an inner face of the rib of the cap and an outer face of the protrusion part of the distal cylindrical part contact with each other, the container or the sheet-shaped lid member includes a ventilation part that has bacteria impermeability and vapor distributability, and the outer cylinder for prefilled syringe is sterilized by high pressure steam in a state of being stored in the outer cylinder packaging for prefilled syringes.

(In one aspect, the outer cylinder for prefilled syringe includes: an outer cylinder main body; and a cylindrical member that is fixed to a tip of the outer cylinder main body. The outer cylinder main body includes: the outer cylinder main body part; the flange part; and the nozzle part. The cylindrical member constitutes the distal cylindrical part that covers the nozzle part, and a proximal part of the cylindrical member is the inclined part that is inclined toward the outer cylinder main body part.

In the above-described outer cylinder packaging for prefilled syringes, because the cylindrical member that is different from the outer cylinder main body constitutes the distal cylindrical part, the inclined part can be provided easily even in the case where it is difficult to manufacture the outer cylinder main body and the distal cylindrical part as an integral product.

In one aspect, the outer cylinder for prefilled syringe is an integral product that includes the outer cylinder main body part, the flange part, the nozzle part, the distal cylindrical part, and the inclined part.

In the above-described outer cylinder packaging for prefilled syringes, because the distal cylindrical part and the inclined part are constituted as the integral product with the outer cylinder main body part, the flange part, and the nozzle part, it is possible to reduce the manufacturing cost by the simplification and the like of the manufacturing processes of the outer cylinder packaging for prefilled syringes that is provided with the inclined part.

According to one embodiment, an outer cylinder for prefilled syringe is configured to be stored in a container of which an upper face has an opening; an outer cylinder holding member that is stored in the container and has many outer cylinder holding opening parts; and a sheet-shaped lid member that seals the upper face opening of the container and can be peeled off, the outer cylinder for prefilled syringe being used for an outer cylinder packaging for prefilled syringes to be sterilized. The outer cylinder for prefilled syringe further includes: an outer cylinder main body part; a flange part that is provided at a proximal part of the outer cylinder main body part, protrudes outward, and cannot pass through the outer cylinder holding opening part; a nozzle part that is provided at a tip part of the outer cylinder main body part and has a tip opening part at its tip; and a distal cylindrical part which covers the nozzle part, has a diameter that is larger than an outer diameter of the outer cylinder main body part and can pass through the outer cylinder holding opening part. The outer cylinder for prefilled syringe can be inserted from a distal into the outer cylinder holding opening part of the outer cylinder holding member, and has an inclined part which is positioned at a proximal part of the distal cylindrical part and is inclined in a proximal direction from an outer edge of the distal cylindrical part toward an outer peripheral face of the outer cylinder main body part so as to guide the outer cylinder for prefilled syringe to be withdrawn from the outer cylinder holding opening part.

In one aspect, the outer cylinder for prefilled syringe includes a cap that is attached to a tip part of the outer cylinder for prefilled syringe and seals the tip opening part of the nozzle part, another medical instrument can be connected to the nozzle part, the distal cylindrical part includes, on its inner peripheral face, a cylindrical part-side screw part that can be screwed with the medical instrument which is to be connected to the nozzle part, and the cap can pass through the outer cylinder holding opening part.

In one aspect, the distal cylindrical part includes: a cylindrical main body part; and an annular proximal part that is positioned at a proximal of the cylindrical main body part. The inclined part is formed of a proximal face of the annular proximal part, an outer edge of a tip part of the annular proximal part protrudes outward more than an outer peripheral face of the cylindrical main body part, and the cap includes an attachment part that covers the outer peripheral face of the cylindrical main body part.

In one aspect, the attachment part of the cap includes: an outside cylindrical part that covers the outer peripheral face of the cylindrical main body part; and an inside cylindrical part which is positioned inside the outside cylindrical part and has a cap-side screw part that can be screwed with the cylindrical part-side screw part. The cap includes: a sealing member that is stored in the inside cylindrical part and seals an opening of the nozzle part; and a rib that is formed on an inner face of the outside cylindrical part. The cap is attached to a tip part of the outer cylinder for prefilled syringe by screwing between the cylindrical part-side screw part and the cap-side screw part, the distal cylindrical part includes a protrusion part that is provided on the outer peripheral face of the cylindrical main body part, and the cap prevents looseness between the rib and the protrusion part by a contact between the rib and the protrusion part in a state where the cap is attached to the outer cylinder for prefilled syringe.

What is claimed is:

1. An assembly of an outer cylinder packaging and an at least one outer cylinder configured to be filled with a medicinal solution, stored in the outer cylinder packaging, the assembly comprising:
   a container having an upper face that has an upper face opening;
   an outer cylinder holding member that is located in the container and includes at least one outer cylinder holding opening part;
   at least one outer cylinder configured to be filled with a medicinal solution, the at least one outer cylinder being held by the outer cylinder holding member; and
   a removable sheet-shaped lid member that seals the upper face opening of the container,
   wherein the at least one outer cylinder includes:
      an outer cylinder main body part;
      a flange part that is provided at a proximal part of the outer cylinder main body part, protrudes outward, and is not passable through the outer cylinder holding opening part;
      a nozzle part that is provided at a tip part of the outer cylinder main body part and has a tip opening part at its tip; and
      a distal cylindrical part that covers the nozzle part, has a diameter that is larger than an outer diameter of the outer cylinder main body part, and passes through the outer cylinder holding opening part,
   wherein the at least one outer cylinder is located in the at least one outer cylinder holding opening part of the outer cylinder holding member such that the flange part of the at least one outer cylinder is in contact with and suspended by a rim of the at least one outer cylinder holding opening part,
   wherein the at least one outer cylinder includes an inclined part that is positioned at a proximal part of the distal cylindrical part and is inclined in a proximal direction from an outer edge of the distal cylindrical part toward an outer peripheral face of the outer cylinder main body part,
   wherein the inclined part extends to a position in a vicinity of the outer peripheral face of the outer cylinder main body part, and
   wherein the inclined part is configured such that, when the at least one outer cylinder is withdrawn from the at least one outer cylinder holding opening part, the inclined part contacts a surface of the at least one outer cylinder holding opening part so as to guide the at least one outer cylinder as the at least one outer cylinder is withdrawn from the at least one outer cylinder holding opening part, without becoming caught on the at least one outer cylinder holding opening part.

2. The assembly according to claim 1,
   wherein the at least one outer cylinder further includes a cap that is attached to a tip part of the outer cylinder and that seals the tip opening part of the nozzle part,
   wherein the nozzle part is configured such that a medical instrument is connectable thereto,
   wherein the distal cylindrical part further includes, on its inner peripheral face, a cylindrical part-side screw part that is screwably connectable to the medical instrument that is to be connected to the nozzle part, and
   wherein the cap is passable through the outer cylinder holding opening part.

3. The assembly according to claim 2,
   wherein the distal cylindrical part further includes:
      a cylindrical main body part; and
      an annular proximal part that is positioned proximal of the cylindrical main body part,
   wherein the inclined part is formed of a proximal face of the annular proximal part,
   wherein an outer edge of a tip part of the annular proximal part protrudes farther outward than an outer peripheral face of the cylindrical main body part, and
   wherein the cap includes an attachment part that covers the outer peripheral face of the cylindrical main body part.

4. The assembly according to claim 3,
   wherein the attachment part of the cap includes:
      an outside cylindrical part that covers the outer peripheral face of the cylindrical main body part; and
      an inside cylindrical part that is positioned inside the outside cylindrical part and has a cap-side screw part on an outer peripheral face of inside cylindrical part, the cap-side screw part being screwably connectable to the cylindrical part-side screw part,
   wherein the cap further includes:
      a sealing member that is located in the inside cylindrical part and configured to seal the tip opening part of the nozzle part; and
      a rib that is formed on an inner face of the outside cylindrical part,
   wherein the cap is configured to be attachable to the tip part of the outer cylinder by screwing together the cylindrical part-side screw part and the cap-side screw part,
   wherein the distal cylindrical part further includes a protrusion part that is provided on the outer peripheral face of the cylindrical main body part, and
   wherein the cap is configured to inhibit looseness between the rib and the protrusion part by way of a contact between the rib and the protrusion part when the cap is attached to the outer cylinder.

5. The assembly according to claim 4,
   wherein, when the cap is attached to the outer cylinder, an inner face of the rib of the cap and an outer face of the protrusion part of the distal cylindrical part contact each other,
   wherein one of the container and the sheet-shaped lid member includes a ventilation part that has bacteria impermeability and vapor distributability, and
   wherein the at least one outer cylinder is sterilizable by high pressure steam while stored in the outer cylinder packaging.

6. The assembly according to claim 1, wherein an outer diameter of a proximal end of the inclined part is approximately equal to an outer diameter of the outer peripheral face of the outer cylinder main body part.

* * * * *